(12) United States Patent
Yoshida et al.

(10) Patent No.: US 12,257,030 B2
(45) Date of Patent: Mar. 25, 2025

(54) ELECTRIC TOOTHBRUSH, BRUSH UNIT, AND METHOD FOR OPERATING AN ELECTRIC TOOTHBRUSH

(71) Applicants: Colgate-Palmolive Company, New York, NY (US); Omron Healthcare Co., Ltd., Kyoto (JP)

(72) Inventors: Hideaki Yoshida, Kyoto (JP); Mamoru Katano, Kyoto (JP); Masashi Kitamura, Kyoto (JP); Toshifumi Matsumoto, Kyoto (JP)

(73) Assignees: Colgate-Palmolive Company, New York, NY (US); Omron Healthcare Co., Ltd. (JP)

( * ) Notice: Subject to any disclaimer, the term of this patent is extended or adjusted under 35 U.S.C. 154(b) by 1268 days.

(21) Appl. No.: 16/985,283

(22) Filed: Aug. 5, 2020

(65) Prior Publication Data

US 2020/0359902 A1    Nov. 19, 2020

Related U.S. Application Data

(62) Division of application No. 15/735,335, filed as application No. PCT/US2016/036604 on Jun. 9, 2016, now Pat. No. 10,765,323.

(30) Foreign Application Priority Data

Jun. 12, 2015  (JP) ................................ 2015-119558
Jun. 12, 2015  (JP) ................................ 2015-119559
(Continued)

(51) Int. Cl.
*A61B 5/00*    (2006.01)
*A46B 5/00*    (2006.01)
(Continued)

(52) U.S. Cl.
CPC .......... *A61B 5/0088* (2013.01); *A46B 5/0095* (2013.01); *A46B 9/04* (2013.01);
(Continued)

(58) Field of Classification Search
CPC ............ A46B 15/0034; A46B 15/0036; A46B 15/0044; A46B 9/005; A46B 2200/1066;
(Continued)

(56) References Cited

U.S. PATENT DOCUMENTS 6,485,300 B1 *  11/2002  Muller ................. A61B 5/0088
                                                        433/29
6,862,771 B1 *   3/2005  Muller ............... A46B 15/0002
                                                        15/105

(Continued)

FOREIGN PATENT DOCUMENTS

AU     2015417105      2/2019
CN     101965160      2/2011
(Continued)

OTHER PUBLICATIONS

International Search Report and the Written Opinion of the International Searching Authority issued in International Application PCT/US2016/036604 mailed Nov. 14, 2016.

*Primary Examiner* — Makena S Markman

(57) ABSTRACT

In one embodiment, the invention can be a brush unit detachable from a main body unit of an electric toothbrush. The brush unit includes: a light transmitting part included on a front surface of the brush unit, a plurality of tooth cleaning elements extending from the front surface of the brush unit in a pressing direction, wherein the light transmitting part directs more light in a first direction, which intersects the pressing direction, than in the pressing direction; and a light receiving part included on the front surface for receiving light; wherein the light transmitting part and the light receiving part are arranged on opposing sides of the plurality (Continued)

of tooth cleaning elements; and wherein the first direction lies within a plane including both the light transmitting part and the light receiving part.

15 Claims, 17 Drawing Sheets

(30) Foreign Application Priority Data

Jun. 12, 2015 (JP) .................................. 2015-119560
Jun. 12, 2015 (JP) .................................. 2015-119563

(51) Int. Cl.
*A46B 9/04* (2006.01)
*A46B 15/00* (2006.01)
*A61C 17/34* (2006.01)

(52) U.S. Cl.
CPC ...... *A46B 15/0034* (2013.01); *A46B 15/0036* (2013.01); *A61C 17/34* (2013.01); *A46B 2200/1066* (2013.01)

(58) Field of Classification Search
CPC ... A46B 5/0095; A61B 5/0088; A61B 5/4547; A61C 1/088; A61N 2005/0606; A61N 2005/0644
See application file for complete search history.

(56) References Cited

U.S. PATENT DOCUMENTS

| | | | |
|---|---|---|---|
| 6,902,397 B2* | 6/2005 | Farrell | A46B 15/0002 433/29 |
| 7,886,393 B2 | 2/2011 | Sorrentino | |
| 8,578,544 B2 | 11/2013 | Brown, Jr. et al. | |
| 10,080,632 B2 | 9/2018 | Lee | |
| 10,098,447 B2 | 10/2018 | Newman et al. | |
| 10,390,708 B2 | 8/2019 | Nozaki | |
| 2008/0131834 A1* | 6/2008 | Shepherd | A46B 15/0034 433/29 |
| 2009/0083924 A1* | 4/2009 | Shepherd | A46B 15/0002 15/105 |
| 2011/0200959 A1* | 8/2011 | Rizoiu | A46B 15/0055 433/29 |
| 2011/0296643 A1* | 12/2011 | Shepherd | A61N 5/0603 15/167.1 |
| 2013/0203008 A1* | 8/2013 | Kressman | A61B 5/0071 433/27 |
| 2014/0199651 A1* | 7/2014 | Adachi | A46B 15/0034 433/27 |
| 2015/0283401 A1* | 10/2015 | Cha | A46D 1/0207 433/29 |
| 2015/0305670 A1* | 10/2015 | Spruit | A61C 17/227 433/27 |
| 2018/0236704 A1 | 8/2018 | Oshita et al. | |

FOREIGN PATENT DOCUMENTS

| | | |
|---|---|---|
| CN | 102113765 | 7/2011 |
| CN | 102470532 | 5/2012 |
| CN | 103764063 | 4/2014 |
| CN | 104114081 | 10/2014 |
| JP | 3475793 | 1/2000 |
| JP | 2000-155137 | 6/2000 |
| JP | 4186374 | 9/2001 |
| JP | 2002-522102 | 7/2002 |
| JP | 2008-532619 | 8/2008 |
| JP | 2009-028310 | 2/2009 |
| JP | 2013-042906 | 3/2013 |
| JP | 2014-217598 | 11/2014 |
| KR | 20100010005 | 1/2010 |
| WO | 2013/119776 | 8/2013 |
| WO | 2014/097198 | 6/2014 |
| WO | 2016143974 | 9/2016 |

* cited by examiner

ELECTRIC TOOTHBRUSH, BRUSH UNIT, AND METHOD FOR OPERATING AN ELECTRIC TOOTHBRUSH

CROSS-REFERENCE TO RELATED APPLICATIONS

The present application is a divisional of U.S. patent application Ser. No. 15/735,335, filed Dec. 11, 2017, which is a national phase entry under 35 U.S.C. § 371 of PCT/US2016/036604, filed Jun. 9, 2016, which claims priority under 35 U.S.C. § 119 to Japanese Patent Application No. 2015-119558, filed Jun. 12, 2015, Japanese Patent Application No. 2015-119559, filed Jun. 12, 2015, Japanese Patent Application No. 2015-119560, filed Jun. 12, 2015, and Japanese Patent Application No. 2015-119563, filed Jun. 12, 2015, the disclosures of which are incorporated herein by reference in their entireties.

BACKGROUND

The present invention relates to an electric toothbrush, a brush unit that is removably attachable to the body unit of an electric toothbrush, and a method for operating an electric toothbrush.

A type of electric toothbrush that performs teeth brushing (plaque removal) by applying a quickly oscillating brush to a surface of a tooth is known. It has been proposed that the brush unit of such an electric toothbrush could be provided with a means for sensing plaque, tartar, tooth decay, and the like adhering to the surface of a tooth. Some electric toothbrushes are known which include a light source and a light sensor on or in the brush unit. Light emitted from the light source reflects off the surface of a tooth and is detected by the light sensor, and the user is notified if tooth decay or the like is sensed using the detected light. Known electric toothbrushes with a light source and a light sensor may be deficient in that plaque or the like is not accurately sensed. Thus, a need exists for an electric toothbrush that can improve the sensing accuracy of plaque, tartar, tooth decay, and the like.

BRIEF SUMMARY

The present invention may be directed, in one aspect, to a brush unit detachable from a main body unit of an electric toothbrush, the brush unit including: a light transmitting part included on a front surface of the brush unit, a plurality of tooth cleaning elements extending from a front surface of the brush unit in a pressing direction, wherein the light transmitting part directs more light in a first direction, which intersects the pressing direction, than in the pressing direction; and a light receiving part included on the front surface for receiving light; wherein the light transmitting part and the light receiving part are arranged on opposing sides of the plurality of tooth cleaning elements, and wherein the first direction lies within a plane including both the light transmitting part and the light receiving part.

In another aspect, the invention may be directed to a brush unit including: a front surface; a plurality of tooth cleaning elements coupled to and extending from the front surface in a pressing direction, the tooth cleaning elements forming a bristle field on the front surface; a light transmitting part formed on the front surface adjacent the bristle field; a light receiving part formed on the front surface adjacent the bristle field and on an opposite side of the bristle field from the light transmitting part; and the light transmitting part is configured to direct light transmitted therethrough in a first direction, the first direction intersecting the pressing direction and lying within a plane including both the light transmitting part and the light receiving part.

In another aspect, the invention may be a brush unit including: a front surface; a plurality of tooth cleaning elements coupled to and extending from the front surface in a pressing direction, the tooth cleaning elements forming a bristle field on the front surface; a light emitting element coupled to the front surface adjacent the bristle field; a light receiving element coupled to the front surface adjacent the bristle field and on an opposite side of the bristle field from the light emitting element; and the light transmitting part is positioned at an angle to direct light in a first direction, the first direction intersecting the pressing direction and lying within a plane including both the light emitting element and the light receiving element.

In yet another aspect, the invention may be an electric toothbrush including: a main body including: a drive assembly, the drive assembly configured to generate oscillations; a light emitting element; and a light receiving element; and a brush unit coupled to the main body, the brush unit including: a housing having a front surface; a plurality of tooth cleaning elements coupled to and extending from the front surface in a pressing direction, the tooth cleaning elements forming a bristle field on the front surface; a light transmitting part formed on the front surface adjacent the bristle field; a light receiving part formed on the front surface adjacent the bristle field and on an opposite side of the bristle field from the light transmitting part; and the light transmitting part is configured to direct light emitted from the light emitting element in a first direction, the first direction intersecting the pressing direction and lying within a plane including both the light transmitting part and the light receiving part.

In still another aspect, the invention may be an electric toothbrush, including: an oscillating assembly comprising a plurality of tooth cleaning elements, a light emitting element, and a light receiving element; and a drive assembly which drives the oscillating assembly to oscillate at a first frequency; wherein the light receiving element is fixed on an isolating member having a resonant frequency different from the first frequency.

In a further aspect, the invention may be an electric toothbrush including: a main body including: a stem; a light emitting element; a light receiving element; and a light guide optically coupled to the light emitting element and to the light receiving element; and a brush unit coupled to the main body, the brush unit including: a housing forming a hollow part and having a front surface, the hollow part configured to be seated on the stem of the main body; a plurality of tooth cleaning elements coupled to and extending from the front surface, the plurality of tooth cleaning elements including at least a first tooth cleaning element formed of an optical transmission material and extending to an interior of the housing, wherein when hollow part of the brush unit is seated on the stem of the main body, the light guide is optically coupled to the first tooth cleaning element such that light emitted from the light emitting element is guided out a tip end of the first tooth cleaning element and light received into the tip end of the first tooth cleaning element is guided to the light receiving element.

In a still further aspect, the invention may be an electric toothbrush, including: a brush unit comprising a housing having a hollow part; and a main body comprising a stem, the hollow part of the brush unit being configured to seat on the stem; wherein: the brush unit comprises a front surface and a plurality of tooth cleaning elements extending from the front surface in a pressing direction; at least a first tooth cleaning element of the plurality of tooth cleaning elements is formed of an optical transmission material, the first tooth cleaning element including a fixed end coupled to the front surface of the brush unit and exposed within the hollow part of the brush unit; and the main body unit comprises a light emitting element which emits light, a light receiving element which generates an output signal in response to received light, a light guide which guides light from the light emitting element to the fixed end of the first tooth cleaning element and which guides light from the fixed end of the first tooth cleaning element to the light receiving element, and a processor which receives the output signal from the light receiving element.

In another aspect, the invention may be an electric toothbrush of the present invention including: an oscillating assembly comprising a plurality of tooth cleaning elements extending from a surface in a pressing direction, a light emitting element, and a light receiving element, the light receiving element generating an output signal in response to received light; a drive assembly having a first drive mode and a second drive mode, wherein during the first drive mode, the drive assembly oscillates the oscillating assembly in a first direction parallel to the pressing direction, and during the second drive mode the drive assembly oscillates the oscillating assembly in a second direction, the second direction being different from the first direction; and a processor configured to control light emitted from the light emitting element during the first drive mode and to process the output signal from the light receiving element that is generated during the first drive mode.

In yet another aspect, the invention may be a method for operating an electric toothbrush, the electric toothbrush comprising a drive assembly and an oscillating assembly, the oscillating assembly comprising a plurality of tooth cleaning elements extending from a surface in a pressing direction, a light transmitting element, and a light receiving element, the method comprising: selectively driving the oscillating assembly with the drive assembly in one of a first drive mode and a second drive mode, wherein during the first drive mode, the drive assembly oscillates the oscillating assembly in a first direction parallel to the pressing direction, and during the second drive mode the drive assembly oscillates the oscillating assembly in a second direction, the second direction being different from the first direction; controlling the light emitting element to emit light at least during the first drive mode; and processing an output signal from the light receiving element at least during the first drive mode, the output signal being generated by the light receiving element in response to received light.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
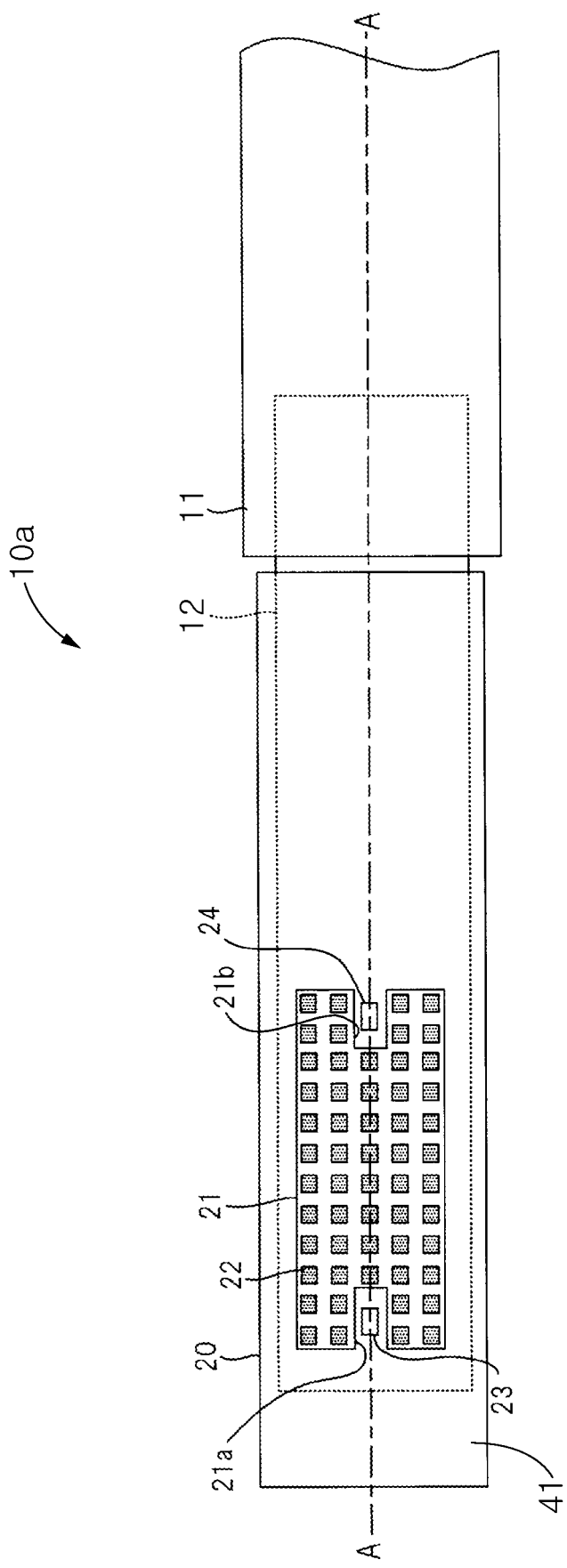
FIG. 1 is a top view of an electric toothbrush in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Figure 2:
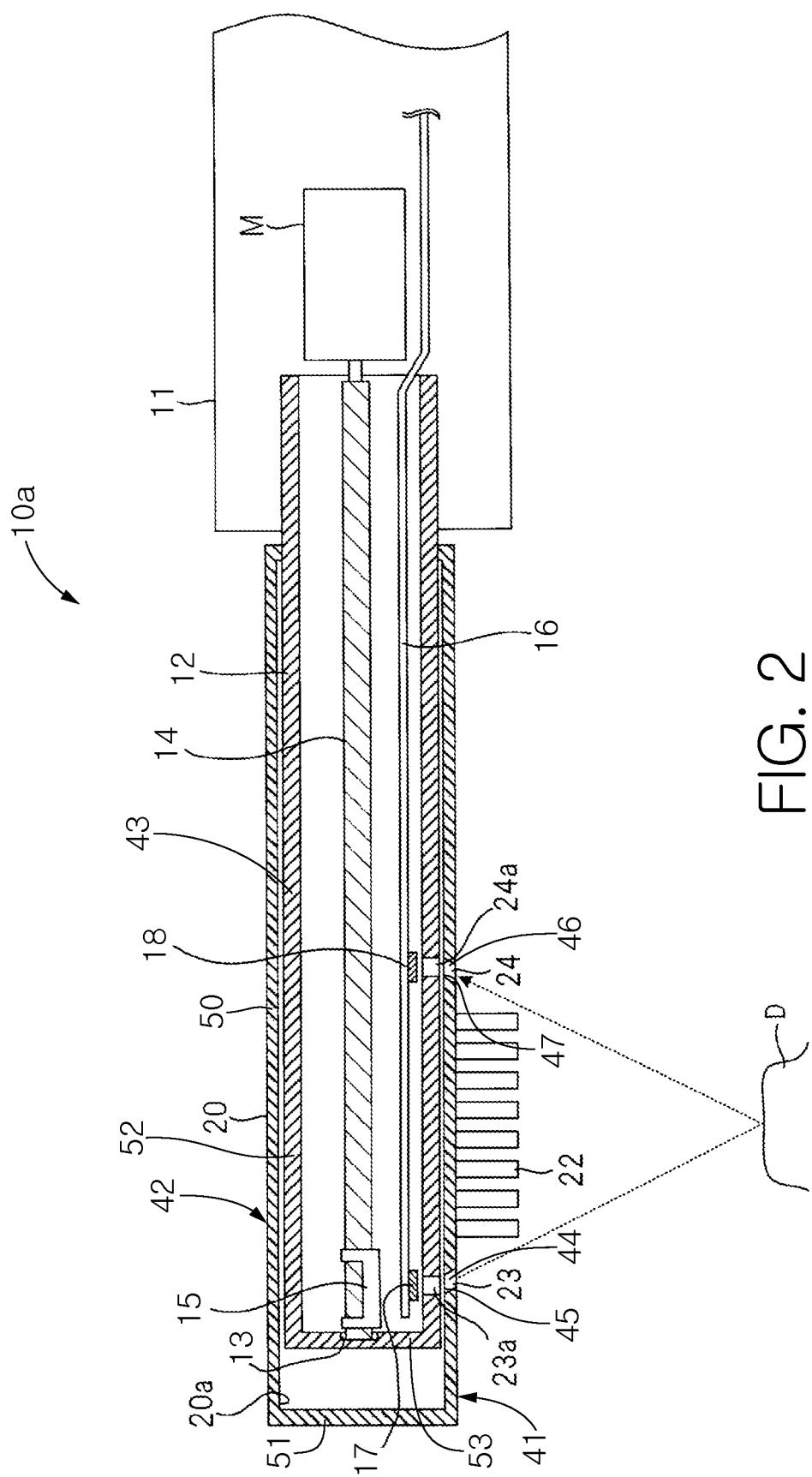
FIG. 2 is a schematic cross sectional view taken along line A-A in FIG. 1.

Referring to FIGS. 1 and 2 concurrently, an electric toothbrush 10*a* (also referred to herein as an oral care implement or a powered toothbrush in some embodiments) is shown in accordance with an embodiment of the present invention. FIG. 1 is a planar view illustrating a schematic configuration of the electric toothbrush 10*a* viewed from the brush pressing direction (the direction that a user presses onto tooth cleaning elements during use), and FIG. 2 is a cross-sectional view taken along line A-A of FIG. 1.

The electric toothbrush 10*a* includes a gripping part 11 that includes a battery and an electric control system therein, as well as a main body having a stem 12 fixed to the gripping part 11, and a brush unit 20 that can be detached from the stem 12. The stem 12 extends from the gripping part 11 and forms the portion of the electric toothbrush 10*a* to which the brush unit 20 may be coupled. Specifically, the brush unit 20 includes an interior cavity 43 that permits the brush unit 20 to be coupled to the stem 12 by inserting the stem 12 into the interior cavity 43. The brush unit 20 may be repetitively coupled to and detached from the stem 12 as necessary or desired. The brush unit 20 and the stem 12 may also include corresponding structures that facilitate locking the brush unit 20 to the stem 12 (a boss and a corresponding notch, an indent and a corresponding detent, or the like). Thus, the gripping part 11 and the stem 12 may be reused with different brush units 20 having different structural arrangements to achieve different purposes. Furthermore, the brush unit 20 may be replaced when the tooth cleaning elements thereon are worn or splayed over time. This saves a user costs because the portion of the electric toothbrush 10*a* that includes the circuitry may be reused while the brush unit 20 which is a simple and cheap component may be replaced. The brush unit 20 may be referred to herein and in the art as a refill head.

The brush unit 20 includes a front surface 41 and an opposite rear surface 42. Furthermore, the brush unit 20 includes a plurality of tooth cleaning elements 22 extending from the front surface 41. The plurality of tooth cleaning elements 22 are depicted in various aligned columns and rows, although the invention is not to be so limited. The number, pattern, configuration, and structure of the tooth cleaning elements 22 is not to be limited in all embodiments. In certain embodiments, the tooth cleaning elements 22 are formed by a plurality of bristles that are bundled together into tufts that are then coupled to a head of the brush unit 20. The tooth cleaning elements 22 may be coupled to the head using staple technology, anchor-free tufting technologies, in-mold tufting technologies, or any other technology now known or later discovered. The tooth cleaning elements 22 may include bristles alone, bristles in combination with lamella formed of an elastomeric material, only bristles formed of an elastomeric material, or the like. The invention is not to be particularly limited by the specific details of the bristles unless specifically claimed as such. As discussed above, in certain embodiments the brush unit 20 may be detachable from the stem 12 and replaceable as needed when the tooth cleaning elements 22 thereon become frayed from use.

The brush unit 20 is also includes a light transmitting part 23 and a light receiving part 24. The light transmitting part 23 and the light receiving part 24 are formed on the front surface 41 of the brush unit 20. In FIG. 1, the brush unit 20 is viewed from a position above the front surface 41, and the direction in which the tooth cleaning elements 22 extend away from the front surface 41 is referred to herein as the "pressing direction" of the tooth cleaning elements 22. As illustrated in FIG. 1, the tooth cleaning elements 22 are arranged in an "H" shape. The outer edge 21 "H" shaped arrangement of the tooth cleaning elements 22 is formed to include a first recess 21*a* and a second recess 21*b*, each of which is respectively included on one of the short sides of the "H" shape. The light transmitting part 23 is positioned within the recess 21*a*, and the light receiving part 24 is positioned on the recess 21*b*.

The light transmitting part 23 is a first transparent window formed by a first transmission member 44 fit into a hole 45 formed in the front surface 41 of the brush unit 20. As described below, the first transmission member 44 transmits light emitted from a light emitting element 17 included as part of the stem 12. Light emitted from the light emitting element 17 is thereby transmitted to the exterior of the brush unit 20 through the light transmitting part 23. Similarly, the light receiving part 24 is a second transparent window formed by a second transmission member 46 fit into a hole 47 in the front surface 41 of the brush unit 20. As described below, the second transmission member 46 transmits light emitted from the light transmitting part 23 and reflected or received from a target object in the mouth (e.g., a tooth). Light that transmits through the second transmission member 46 is incident on a light sensing element 18 included as part of the stem 12.

As shown in the exemplified embodiment, the light transmitting part 23 and the light receiving part 24 are arranged outside the edges of the "H" shape formed by the tooth cleaning elements 22, such that at least a first group 48 of tooth cleaning elements 22 are positioned between the light transmitting part 23 and the light receiving part 24. Both the light transmitting part 23 and the light receiving part 24 also lie on a line which is parallel to the longitudinal dimension of the brush unit 20, however, the invention is not to be so limited unless otherwise stated in the claims. More generally, with regards to the positioning of the light transmitting part 23 and the light receiving part 24, the tooth cleaning elements 22 form a bristle field, and both the light transmitting part 23 and the light receiving part 24 are located external to the bristle field on the front surface 41 of the brush unit 20. In certain embodiments, one or both of the light transmitting part 23 and the light receiving part 24 may be located within the field of tooth cleaning elements 22, or at any other desired location along front surface 41 the brush unit 20, to the extent that the tooth cleaning elements 22 are configured to not interfere with the emitted light. Thus, the invention is not to be particularly limited by the position of the transparent window 23 unless specifically claimed as such.

As is shown in FIG. 2, the brush unit 20 includes a cylindrical housing 50 with the tip end portion 51 being closed to form a hollow part 20a. The stem 12 includes a tube shaped housing 52 with the tip end 53 closed. By fitting the stem 12 into the hollow part 20a, the main body unit and the brush unit 20 may be coupled together. The stem 12 includes a bearing 13 formed on the interior surface of the tip end 53. One end of an eccentric shaft 14 is inserted into the bearing 13, and a weight 15 is coupled to the eccentric shaft 14. The other end of the eccentric shaft 14 is linked to a rotary shaft of the motor M built in the gripping part 11. The motor M, the eccentric shaft 14, and the weight 15 form the drive assembly for generating oscillations. By rotating the rotary shaft of the motor M, the eccentric shaft 14 rotates. The weight 15 is fixed to the eccentric shaft 14 in the vicinity of the bearing 13. Due to this weight 15, the center of gravity of the eccentric shaft 14 is shifted from the center of rotation. Note that a minute clearance is provided between the eccentric shaft 14 and the bearing 13.

Although the eccentric shaft 14 rotates along with the rotation of the rotary shaft of the motor M, since the center of gravity of the eccentric shaft 14 is shifted due rotation of the weight 15, a motion of rotating about the center of rotation is achieved. Thus, the entire eccentric shaft 14 bends, and the stem 12, along with the brush unit 20 coupled to the stem 12, oscillates at a high speed. Thus, the stem 12 and the brush unit 20 form the oscillating assembly of the electric toothbrush 10a. By oscillating the brush unit 20 using rotational movement of the eccentric shaft 14 in this manner, the brush unit 20 effectively oscillates in a direction parallel to the pressing direction of the brush 22 and perpendicular to the rotary shaft of the motor M.

In the exemplified embodiment, the entirety of the oscillating assembly (stem 12 and brush unit 20) has a resonance point (resonance frequency), and can switch between a first operational mode in which the stem 12 and brush unit 20 oscillate in the pressing direction of the tooth cleaning elements 22 and a second operational mode in which the stem 12 and brush unit 20 oscillate in a plane perpendicular to the pressing direction of the tooth cleaning elements 22. The electric toothbrush 10a may switch between the first and second drive modes by controlling the rotary speed of the motor M.

The stem 12 also includes a light emitting element 17 and a light receiving element 18 fixed on a substrate 16, and holes 23a and 24a in the cylindrical housing 50. The hole 23a is positioned on the stem 12 so that when the brush unit 20 is coupled to the stem 12, the hole 23a is positioned adjacent to the light transmitting part 23. Similarly, the hole 24a is positioned on the stem 12 so that when the brush unit 20 is coupled to the stem 12, the hole 24a is positioned adjacent to the light receiving part 24.

The light emitting element 17 includes a light emitting diode (LED), a laser diode, and the like. The invention is not to be so limited, as other types of light generating devices may be used for the light emitting element 17. The wavelength of light emitted from the light emitting element 17 may be appropriately selected according to the elements in the mouth (plaque, tartar, tooth decay, and the like) to be detected. The light emitting element 17 is positioned adjacent the hole 23a in the interior of the stem 12 so that light emitted from the light emitting element 17 passes through the hole 23a.

The light receiving element 18 includes a light sensing element, such as a photo diode or the like, that converts light into an electric signal. The invention is not to be so limited, as other types of light sensing elements may be used for the light receiving element 18. The light receiving element 18 is positioned adjacent the hole 24a in the interior of the stem 12 so that light passing through the hole 24a is incident on the light receiving element 18.

A substrate 16 includes wiring electrically connected to the light emitting element 17 and to the light receiving element 18. In certain embodiments, a flexible substrate may be used as the substrate 16. The substrate 16 extends to the interior of the gripping portion 11, and the wiring formed on the substrate 16 is electrically connected to a controller, described below, which is positioned within the gripping portion 11.

As illustrated in FIG. 2, the cross-sectional shape of the first transmission member 44, which forms part of the light transmitting part 23, has a side wall running in a direction orthogonal to the pressing direction of the tooth cleaning elements 22 and extends in a slanted angle toward the light receiving part 24. With this shape for the first transmission member 44, light emitted from the light emitting element 17 passes through the hole 23a of the stem 12, and then through the first transmission member 44, so that the light is directed toward the light receiving part 24. The light transmitting part 23 therefore emits light in a direction that intersects the pressing direction of the tooth cleaning elements 22, as opposed to emitting light parallel to the pressing direction, so that the emitted light is directed at least partially within a plane defined by the pressing direction and including both the light transmitting part 23 and the light receiving part 24.

Similar to the first transmission member 44, the cross-sectional shape of the second transmission member 45, which forms part of the light receiving part 24, has a side wall running in a direction orthogonal to the pressing direction of the tooth cleaning elements 22 and extends in a slanted angle toward the light transmitting part 23. With this shape for the second transmission member 45, light emitted by the light transmitting part 23 that is reflected by, for example, a tooth D, is received through the second transmission member 45, as opposed to the second transmission member 45 receiving light from the pressing direction of the tooth cleaning elements 22.

In certain embodiments, the side wall slant angle and distance from the tooth cleaning elements 22 of the first transmission member 44 may be determined so that light emitted from the light transmitting part 23 has no vignetting from the tooth cleaning elements 22 prior to being directed toward the light receiving part 24. Similarly, in certain embodiments, the side wall slant angle and distance from the tooth cleaning elements 22 of the second transmission member 46 may be determined so that light emitted from the light transmitting part 23 has no vignetting from the tooth cleaning elements 22 after reflecting off a tooth D and prior to passing through the second transmission member 45.

Figure 3:
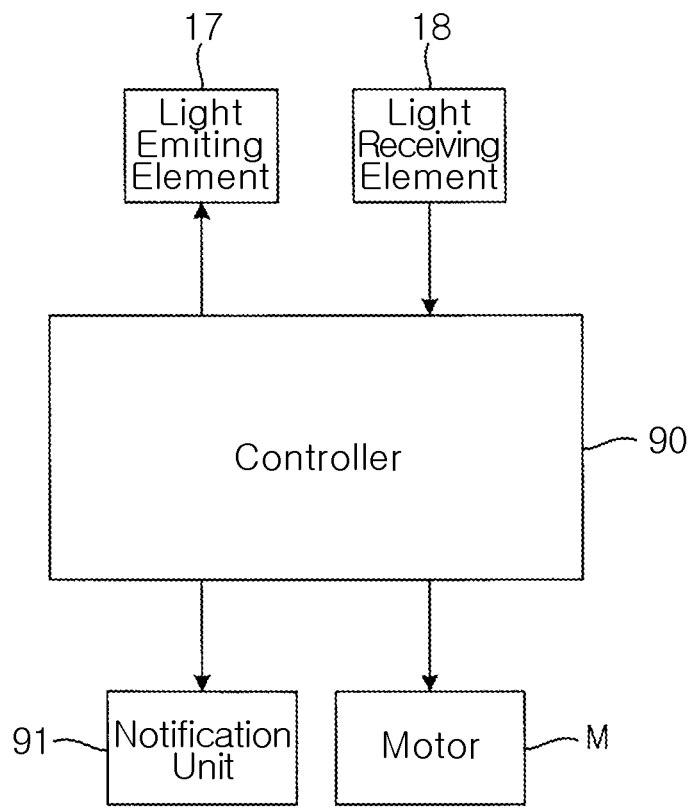
FIG. 3 is a block diagram schematically illustrating an internal configuration of the electric toothbrush of FIG. 1.

As shown in FIG. 3, the gripping portion 11 includes a motor M, a controller 90, and a notification unit 91. The controller 90 controls the motor M to selectively drive the oscillating assembly, which is made up of the stem 12 and the brush unit 20 fixed thereon, in one of a first drive mode or a second drive mode. In the first drive mode, the oscillating assembly oscillates in a first direction that is parallel to the pressing direction of the tooth cleaning elements 22, and in the second drive mode, the oscillating assembly oscillates in a second direction that is different from the pressing direction. The controller 90 switches between the first drive mode and the second drive mode by changing the rotary speed of the rotary shaft of the motor M.

In certain embodiments, the controller 90 may alternately switch between the first drive mode and the second drive mode. By automatically switching the oscillating direction of the brush unit 20, a plaque removal effect can be achieved that excels when compared with brushing in only one direction. This improved plaque removal effect is due to, at least in part, the ends of the tooth cleaning elements 22 touching the teeth (and gums) from various angles while the electric toothbrush 10a is in use, so that the switching of the oscillating direction changes the manner in which the ends of the tooth cleaning elements 22 touch the teeth (and gums). The driving method of the stem 12 by the controller 90 is not intended to limit the scope of the invention unless otherwise stated in the claims. For example, in certain embodiments, only the first drive mode may be performed, and in certain other embodiments, only the second drive mode may be performed. In certain other embodiments, the timing of switching between the first and second drive modes may be varied.

The controller 90 drives the light emitting element 17, via electrical conductors included as part of the substrate 16, and controls the manner in which light is emitted from the light emitting element 17 (e.g., always on, pulsed, pulse timing, and the like). The controller 90 also processes the output signal from the light receiving element 18, with the signal output being received by the controller form electrical conductors included as part of the substrate 16. The signal output from the light receiving element 18 is processed to determine a value of the output signal in order to determine one or more of the following: the amount of plaque adhering to a tooth, whether tartar is present on a tooth, whether tooth decay is present on a tooth, and the like. By way of example, the manner in which the controller 90 processes the output signal to calculate the amount of plaque present on a tooth is described in greater detail.

The notification part 91 notifies the user of the electric toothbrush 10a using a notification device such as a speaker or a light emitting diode (LED). Other types of notification devices may be used, as the invention is not to be so limited. Thus, in certain embodiments, the notification unit 91 follows commands from the controller 90, and notifies the user by making a sound or lighting an LED. The content of the notification may include the amount of plaque identified by the controller 90. For example, the notification unit 91 may inform the user as to the amount of plaque identified by lighting an LED in a green color if the amount of plaque is extremely low, or by lighting an LED in a red color if there is a significant amount of plaque present. By providing different notifications identifying the amount of plaque present, the electric toothbrush 10a helps to support effective teeth brushing.

The operation of the electric toothbrush 10a configured as described above will now be described. When the power of the electric toothbrush 10a is set to on and a brushing start operation is performed, the controller 90 alternately performs the first drive mode and the second drive mode. By this, the brush unit 20 pressed against one or more teeth alternately repeats an oscillation in the first direction followed by an oscillation in the second direction, so that plaque adhering to the tooth may be removed by the tooth cleaning elements 22. Also following the brushing start operation, the controller 90 controls the light emitting element 17 so that light is emitted while the first drive mode and second drive mode are alternately being performed. After light emitted from the light emitting element 17 passes through the hole 23a, it is emitted in a diagonal direction from the light transmitting part 23. Light emitted from the light transmitting part 23 is incident on the tooth D (or more than one tooth) where the plurality of tooth cleaning elements 22 are pressed, and may be reflected off the surface of the tooth D. In certain embodiments, light incident on the surface of the tooth D may induce (through stimulated emission or fluorescence) another wavelength of light to be emitted from a substance, such as plaque, present on the surface of the tooth D. Such an induced emission may occur when, for example, the light transmitting part 23 emits a blue light and plaque is present on the tooth D, so that the light emitted by the plaque is a red light. In the remainder of the discussion below, it is to be understood that where light reflecting off a tooth D is discussed, that such induced emissions may also be present and detected separately or simultaneously. Light, whether reflected or from induced emission, from the tooth D enters the light receiving part 24, passes through the hole 24a, and is received in the light receiving element 18. The light receiving element 18 converts the received light into an electric signal, which forms the output signal received by the controller 90. The controller 90 determines an amount of plaque on the brushed portion of the tooth D by processing the output signal from the light receiving element 18. Then, the controller 90 notifies the user through the notification part 91 to inform the user about the determined amount of plaque.

In the exemplified embodiment shown in FIGS. 1-3, a large portion of light from the light emitting element 17 is emitted from the light transmitting part 23 in a direction that intersects the pressing direction in which the tooth cleaning elements 22 extend. This direction heads from the light transmitting part 23 toward the light receiving part 24 in the planar view of FIG. 1. Therefore, plaque on a surface opposing the front surface 41 where the tooth cleaning elements 22 are formed (e.g., tooth D where the plurality of tooth cleaning elements 22 contact while brushing teeth) can be accurately detected.

Furthermore, in the exemplified embodiment shown in FIGS. 1-3, it is possible for the light receiving part 24 to receive light coming from a direction that intersects the pressing direction in which the tooth cleaning elements 22 extend. This direction heads from the light transmitting part 23 toward the light receiving part 24 in the planar view of FIG. 1. Because of this, a large portion of light emitted from the light emitting element 17 which is reflected by the tooth D may be received by the light receiving element 18. Consequently, the amount of signal output from the light receiving element 18 may be increased, and detection sensitivity of plaque can be raised.

In this manner, the user of the electric toothbrush 10a is accurately informed in real time by the notification unit 91 about the amount of plaque on a tooth being brushed by the tooth cleaning elements 22. Because of this, it becomes possible to perform more effective tooth brushing. Furthermore, detection accuracy of plaque at a site being brushed is improved by light being emitted diagonally from the light transmitting part 23, even when the distance between the light transmitting part 23 and the light receiving part 24 is large. When the distance between the light transmitting part 23 and the light receiving part 24 is close, a region where the density of the tooth cleaning elements 22 becomes coarse becomes larger. However, according to the exemplified embodiment in FIG. 1, because the light transmitting part 23 and the light receiving part 24 are separately, the region where the density of the tooth cleaning elements 22 becomes coarse is dispersed. As a result, the plaque detection capabilities of the electric toothbrush 10a are not significantly reduced, if at all, by the tooth cleaning elements 22.

In embodiments in which the distance between the light transmitting part 23 and the light receiving part 24 in the brush unit 20 is large, the light transmitting part 23 and the light receiving part 24 can be arranged as much on an edge of the front surface 41 of the brush unit 20, where the tooth cleaning elements 22 are formed. In such embodiments, the number of tooth cleaning elements 22 can be increased, and plaque removing abilities can be improved.

In the exemplified embodiment shown in FIG. 1, each of the light transmitting part 23 and the light receiving part 24 are arranged in a location on the front surface 41 of the brush unit 20 so that each is surrounded on three sides by the tooth cleaning elements 22. With such an arrangement, the brush unit 20 can be made smaller when compared with each of the light transmitting part 23 and the light receiving part 24 being arranged outside of the respective recesses formed by the arrangement of the tooth cleaning elements 22. Moreover, by the arrangement shown in FIG. 1, the distance between the light transmitting part 24 and the light receiving part 24 may be made smaller, and the detection accuracy of plaque and the like can be improved.

Furthermore, the brush unit 20 in the exemplified embodiment has a limited number of parts coupled to the housing, including the tooth cleaning elements 22, the first transmission member 44, and the second transmission member 45. Because of this, manufacturing costs can be reduced. Moreover, because the brush unit 20 may be disposable, the benefits of reducing manufacturing costs are very large.

Although the exemplified embodiment is shown with the eccentric shaft 14 and the weight 15 to generate the oscillations in either of the first direction or the second direction, the invention is not to be so limited. For example, in certain embodiments, the oscillations may be generated by a configuration that can integrally oscillate the stem 12 and the brush unit 20 in the first direction and the second direction. For example, it may be a configuration that oscillates the oscillating assembly in the first direction and the second direction by sonic wave oscillation.

Figure 4:
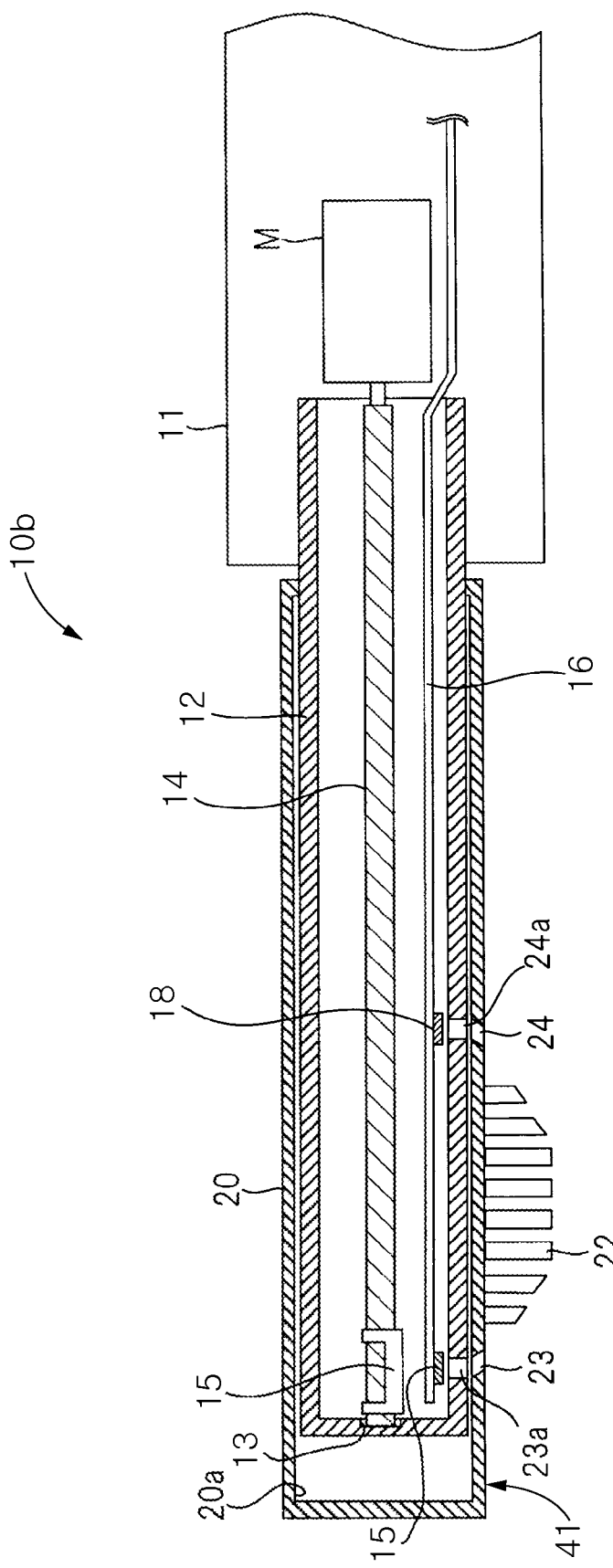
FIG. 4 is a schematic cross sectional view of an electric toothbrush in accordance with a second embodiment of the present invention.

FIG. 4 shows a cross section of another exemplified embodiment of an electric toothbrush 10*b*. In FIG. 4, the same numerals are given to similar components as those shown and described in conjunction with FIGS. 1-3, and the descriptions of such similar components are omitted. In this embodiment of the electric toothbrush 10*b*, the shape of the bristle field formed by the tooth cleaning elements 22 is different, as is the positions of the light transmitting part 23 and the light receiving part 24 with respect to the tooth cleaning elements 22. Within the bristle field, the tooth cleaning elements 22 nearest the light transmitting part 23 and those nearest the light receiving part 24 are shorter than those tooth cleaning elements closer to the middle portion of the bristle field. By way of specific example, eight teeth cleaning elements 22 are illustrated in FIG. 4, and the shape that connects each top face, each bottom face, the right side face of the rightmost brush 22, and the left side face of the leftmost brush 22 is a shape with two corners of the rectangle cut. In other words, the free ends of the tooth cleaning elements 22 nearest both the light transmitting part 23 and the light receiving part 24 are truncated at an angle.

Figure 5:
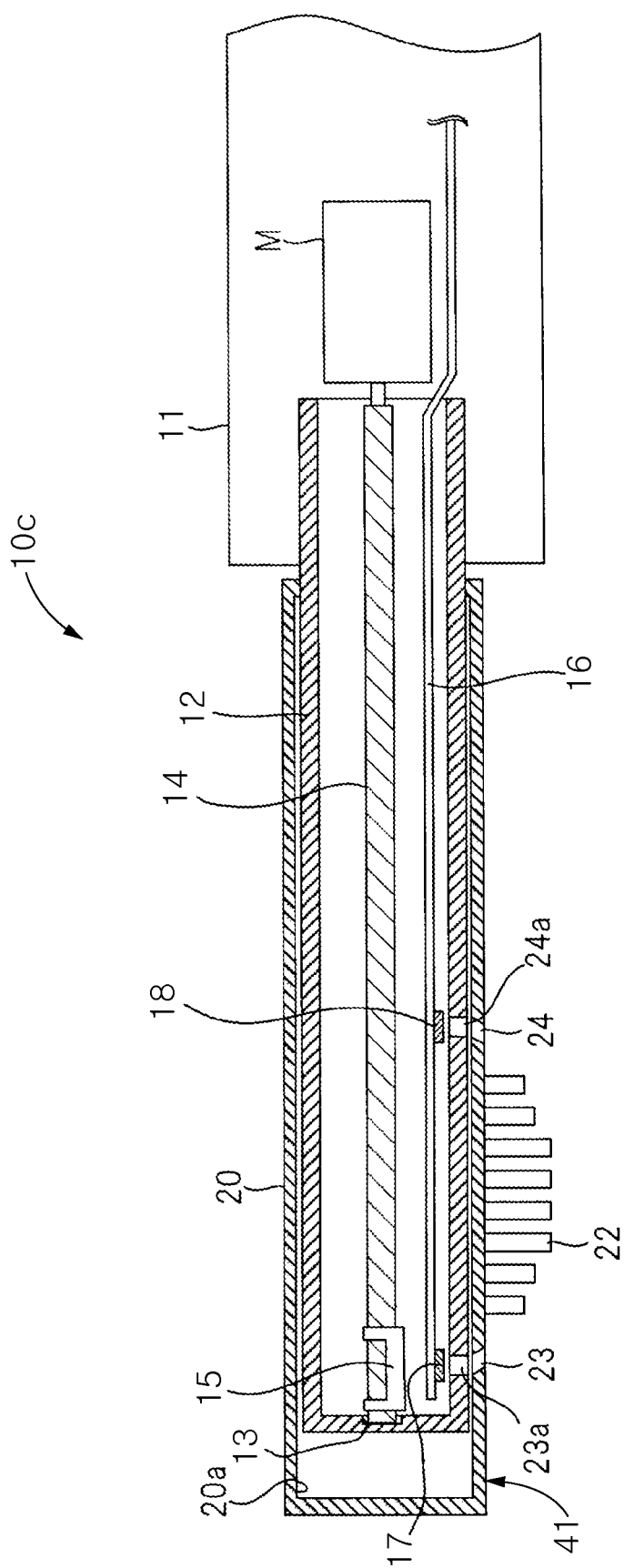
FIG. 5 is a schematic cross sectional view of an electric toothbrush in accordance with a third embodiment of the present invention.

FIG. 5 shows a cross section of another exemplified embodiment of an electric toothbrush 10*c*. In FIG. 5, the same numerals are given to similar components as those shown and described in conjunction with FIGS. 1-3, and the descriptions of such similar components are omitted. In this embodiment of the electric toothbrush 10*c*, the shape of the bristle field formed by the tooth cleaning elements 22 is different, as is the positions of the light transmitting part 23 and the light receiving part 24 with respect to the tooth cleaning elements 22. Within the bristle field, the tooth cleaning elements 22 nearest the light transmitting part 23 and those nearest the light receiving part 24 are shorter than those tooth cleaning elements closer to the middle portion of the bristle field. By way of specific example, eight teeth cleaning elements 22 are illustrated in FIG. 5, the height of the four teeth cleaning elements 22 in the center are the highest, and the teeth cleaning elements 22 become shorter heading toward the light transmitting part 23 from these four teeth cleaning elements 22 in the center. Similarly, the height of the teeth cleaning elements 22 becomes shorter heading toward the light receiving part 24 from these four teeth cleaning elements 22 in the center.

The configuration of the teeth cleaning elements 22 illustrated in FIG. 4 can be one in which, as compared to the eight teeth cleaning elements 22 illustrated in FIG. 5, the free ends of the two teeth cleaning elements 22 closest to the light transmitting part 23 are slanted along the emitting direction of light emitted from the light transmitting part 23, and the free ends of the two teeth cleaning elements 22 closest to the light receiving part 24 are slanted along the progressing direction of light emitted from the light transmitting part 23 and reflected toward the light receiving part 24.

By forming the teeth cleaning elements between the light transmitting part 23 and the light receiving part 24 in the configurations shown in the embodiments of FIGS. 4 and 5, vignetting by the teeth cleaning elements 22 is significantly reduced, if not eliminated, for light emitted from the light transmitting part 23 toward the tooth. Similarly, vignetting by the teeth cleaning elements 22 is significantly reduced, if not eliminated, for light reflecting off the tooth and heading toward the light receiving part 24. Therefore, by these configurations, plaque detection accuracy may be improved.

Figure 6:
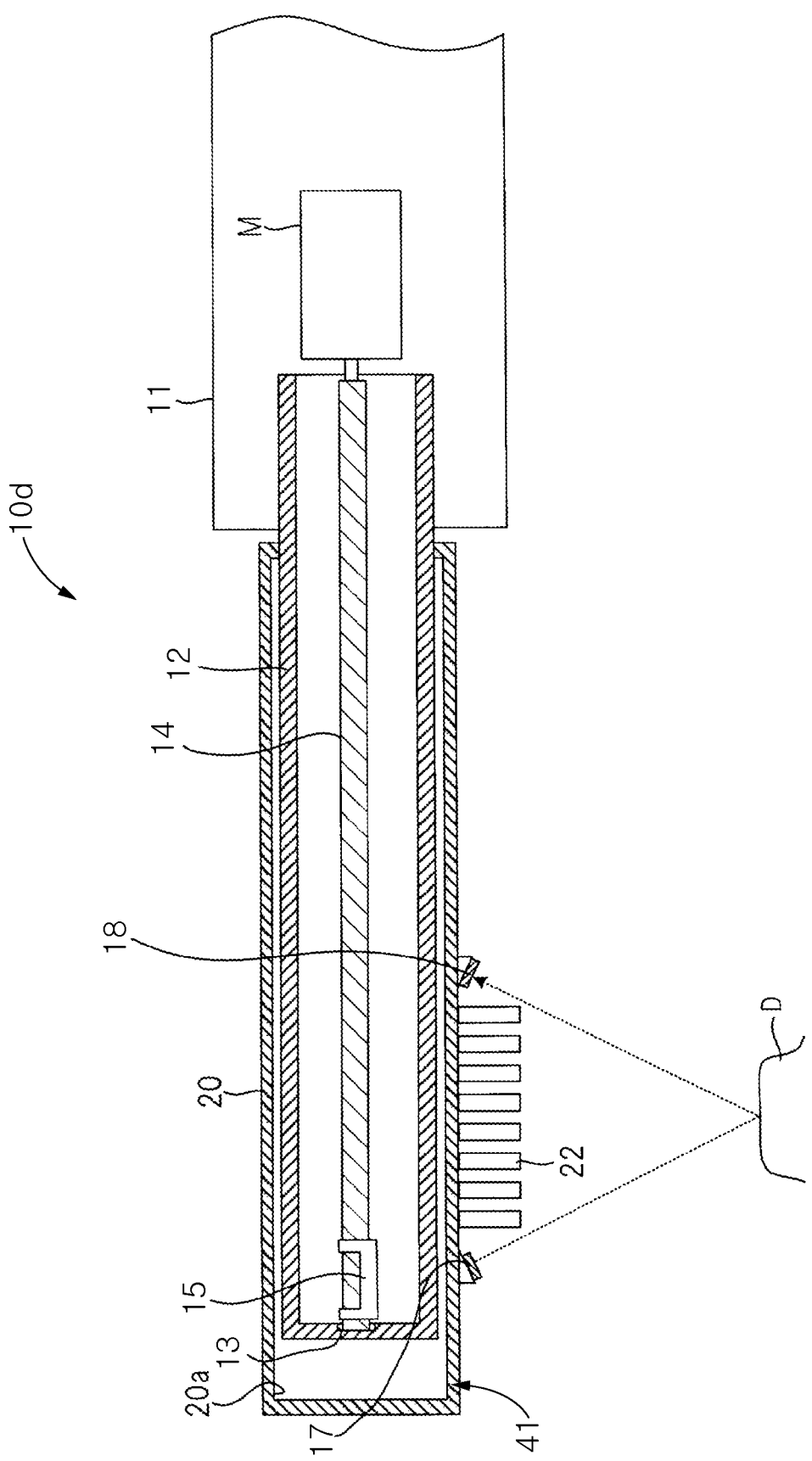
FIG. 6 is a schematic cross sectional view of an electric toothbrush in accordance with a fourth embodiment of the present invention.

Configurations of an electric toothbrush have so far been described in which the light emitting element 17 and the light receiving element 18 are included on the stem 12. However, in certain embodiments, the light emitting element 17 and the light receiving element 18 may be included on the front surface 41 where the teeth cleaning elements 22 of the brush unit 20 are formed. FIG. 6 shows a cross section of another exemplified embodiment of an electric toothbrush 10*d*. In FIG. 6, the same numerals are given to similar components as those shown and described in conjunction with FIGS. 1-3, and the descriptions of such similar components are omitted. In this embodiment of the electric toothbrush 10*d*, the positions and arrangements of the light emitting element 17 and the light receiving element 18 are different. Specifically, in this embodiment, the light emitting element 17 and the light receiving element 18 are positioned on the front surface 41 of the brush unit 20, so that both the light emitting element 17 and the light receiving element 18 are external to the housing of the brush unit 20. The positional arrangement of the light emitting element 17 on the front surface 41, with respect to the bristle field of the teeth cleaning elements 22, is the same as the positional arrangement of the light transmitting part 23 in FIG. 1. Similarly, the positional arrangement of the light receiving element 18 on the front surface 41, with respect to the bristle field of the teeth cleaning elements 22, is the same as the positional arrangement of the light receiving part 24 in FIG. 1.

As illustrated in FIG. 6, the light emitting element 17 is arranged at an angle so that the light emitting face is directed partially in the direction of the light receiving element 18, on the opposite side of the bristle field of the teeth cleaning elements 22, and partially in the direction of the pressing direction of the teeth cleaning elements 22. Similarly, the light receiving element 18 is arranged at an angle so that the light receiving face is directed partially in the direction of the light emitting element 17, on the opposite side of the bristle field of the teeth cleaning elements 22, and partially in the direction of the pressing direction of the teeth cleaning elements 22. The angles at which the light emitting element 17 and the light receiving element 18 may vary, and are not intended to limit the invention unless so stated in the claims.

With the configuration of this exemplified embodiment, the light emitting element 17 emits light in a direction that intersects the pressing direction of the teeth cleaning elements 22, rather than in a direction that is parallel to the pressing direction of the teeth cleaning elements 22, so that the emitted light is directed toward the light receiving element 18. In addition, the by arranging the light receiving element 18 at an angle, more light that is emitted by the light emitting element 17 and reflected off a tooth is received by the light receiving element 18.

In the exemplified embodiment of FIG. 6, the light emitting element 17 fulfills the same function as the light transmitting part 23 of FIG. 1, and the light receiving element 18 fulfills the same function as the light receiving part 24 of FIG. 1. Therefore, in this exemplified embodiment, plaque and the like on a tooth can be accurately detected during brushing.

Figure 7:
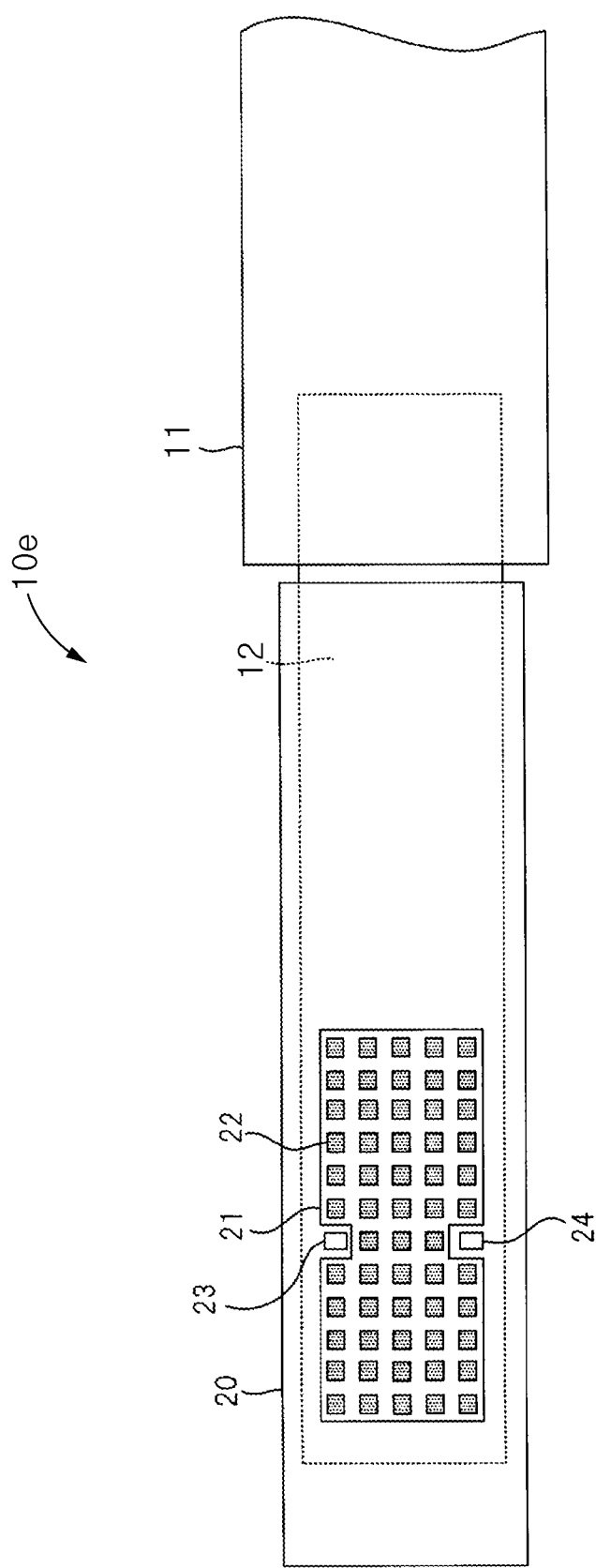
FIG. 7 is a top view of an electric toothbrush in accordance with a fifth embodiment of the present invention.

FIG. 7 shows a top planar of another exemplified embodiment of an electric toothbrush 10*e*. In FIG. 7, the same numerals are given to similar components as those shown and described in conjunction with FIG. 1, and the descriptions of such similar components are omitted. In this embodiment of the electric toothbrush 10*e*, the positions of the light transmitting part 23 and the light receiving part 24 are different with respect to the bristle field formed by the teeth cleaning elements 22. Specifically, the recesses are included on each of two long sides of the outer edge 21 of the bristle field, and the light transmitting part 23 and the light receiving part 24 are each positioned within one of the recesses, respectively. The same improvements as the electric toothbrush 10*a* in FIG. 1 can be obtained with this alternative configuration.

It has been noted that when teeth are being brushed pressing the teeth cleaning elements 22 to a tooth, the teeth cleaning elements 22 may collapse toward the short direction of the brush unit 20. However, during use of the electric toothbrush 10*e*, the teeth cleaning elements 22 only collapse from one direction on each of the light transmitting part 23 and the light receiving part 24. Because of this, the plaque detection capabilities of the electric toothbrush 10*e* are not significantly reduced, if at all, due to collapsing of the tooth cleaning elements 22.

Figure 8:
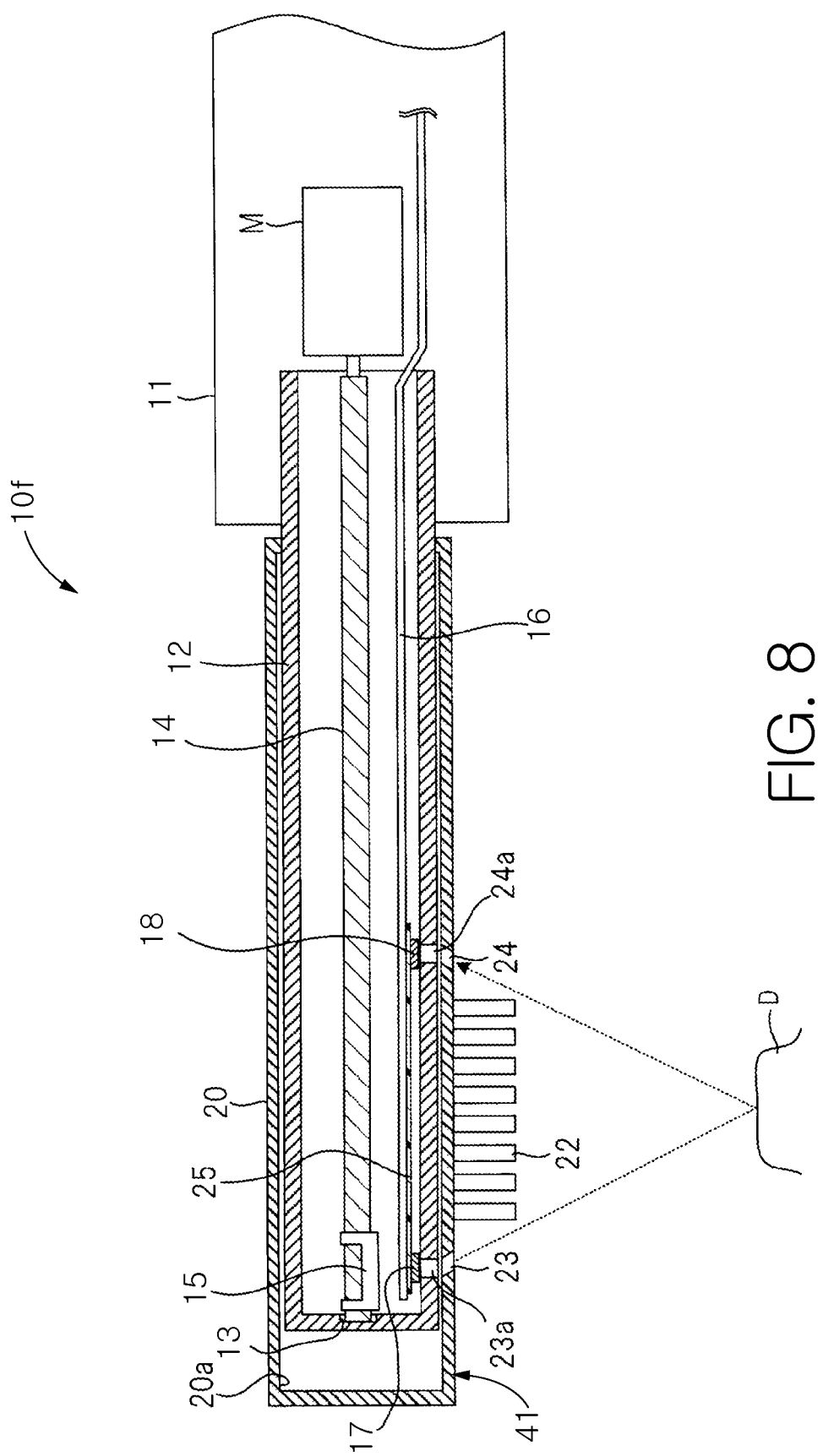
FIG. 8 is a schematic cross sectional view of an electric toothbrush in accordance with a sixth embodiment of the present invention.

FIG. 8 shows a cross section of another exemplified embodiment of an electric toothbrush 10*f*. In FIG. 8, the same numerals are given to similar components as those shown and described in conjunction with FIGS. 1-3, and the descriptions of such similar components are omitted. In this embodiment of the electric toothbrush 10*f*, the light emitting element 17 and the light receiving element 18 are fixed on an isolating member 25, and the isolating member 25 is fixed to the substrate 16.

The isolating member 25 may be formed from a material having a resonant frequency different from one or both of the oscillation frequencies of the first drive mode and the second drive mode for driving the oscillating assembly (stem 12 and brush unit 20) by rotation of the motor M. In certain embodiments, the isolating member 25 may be, for example, urethane. As such, it is understood that the isolating member 25 does not wholly isolate the light emitting element 17 and the light receiving element 18 from all vibrations; rather, the isolating member 25 dampens vibrations present in the oscillating part so that those vibrations have a reduced impact on the light emitting element 17 and the light receiving element 18.

With the electric toothbrush in FIG. 2, the control unit 50 driving the motor M, and thus also the eccentric shaft 14 and weight 15, the light emitting element 17 and the light receiving element 18 are also subject to high speed oscillations. Because of this, there is a possibility that these oscillations will reduce the detection accuracy of plaque. Furthermore, the brush unit 20 is configured so that the distance of the light transmitting part 23 and the light receiving part 24 can be made larger, with the light transmitting part 23 and the light receiving part 24 arranged on opposite sides of the bristle field formed by the teeth cleaning elements 22. The increased distance may result in a time lag occurring between the time light is emitted from the light emitting element 17 and the time the reflected light is received by the light receiving element 18, and this time lag may further contribute to a reduction in detection accuracy of plaque in combination the oscillations.

With the exemplified embodiment shown in FIG. 8, because the light emitting element 17 and the light receiving element 18 are fixed on the isolating member 25, the vibratory motion of the light emitting element 17 and the light receiving element 18 can be reduced even when the oscillating assembly is oscillating. Because of this, improved endurance of the electric toothbrush and improved detection accuracy of plaque can be expected.

Note that in FIG. 8, the light emitting element 17 and the light receiving element 18 are fixed on the isolating member 25, however in certain embodiments, only the light receiving element 18 may be fixed on isolating member 25, and with the light emitting element 17 fixed as described above in FIG. 2. Because the effects of oscillation are higher for the light receiving element 18, it may be so that at least the light receiving element 18 is fixed on the isolating member 25.

Figure 9:
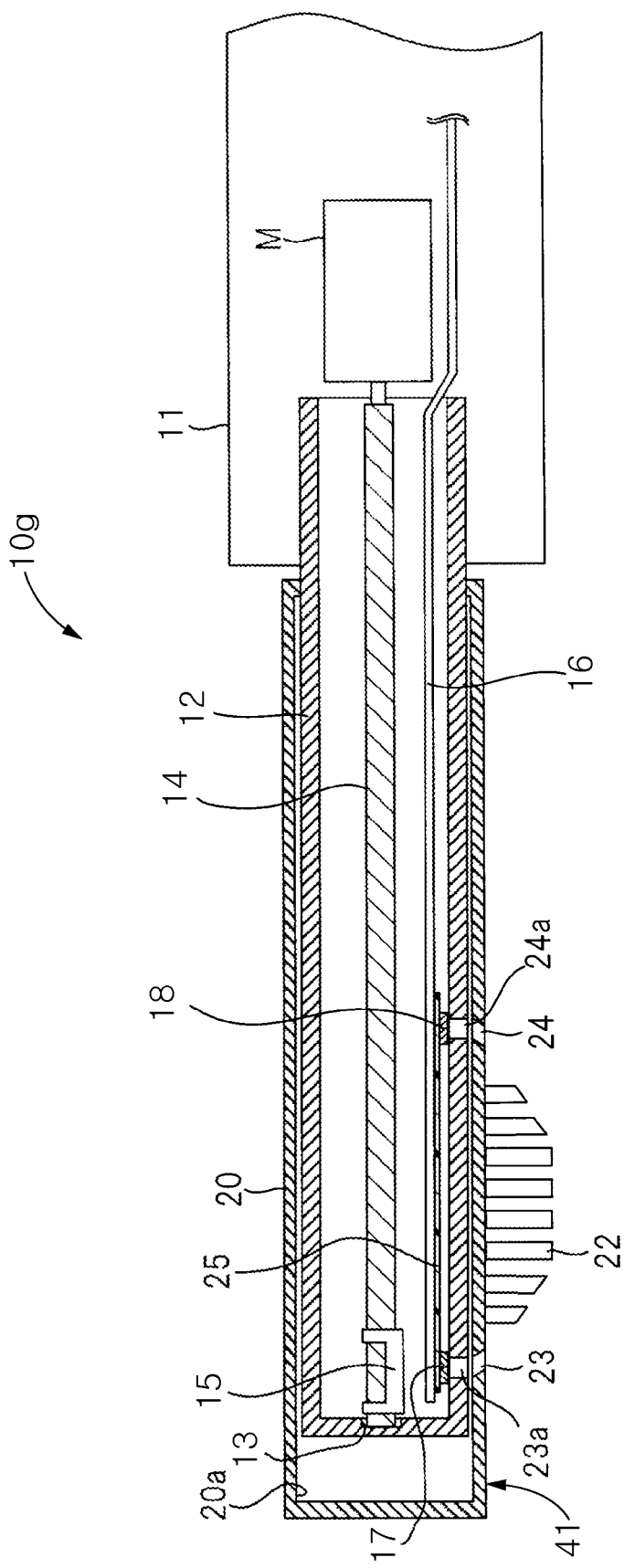
FIG. 9 is a schematic cross sectional view of an electric toothbrush in accordance with a seventh embodiment of the present invention.

FIG. 9 shows a cross section of another exemplified embodiment of an electric toothbrush 10*g*. In FIG. 9, the same numerals are given to similar components as those shown and described in conjunction with FIG. 4, and the descriptions of such similar components are omitted. In this embodiment of the electric toothbrush 10*g*, the light transmitting part 23 and the light receiving part 24 are fixed on the isolating member 25, and the isolating member 25 is fixed to the substrate 16 in a similar manner as described above for the embodiment shown in FIG. 8. In this embodiment of the electric toothbrush 10*g*, the shape of the bristle field formed by the tooth cleaning elements 22 is formed so that the tooth cleaning elements 22 nearest the light transmitting part 23 and those nearest the light receiving part 24 are shorter than those tooth cleaning elements closer to the middle portion of the bristle field, in a manner such as is described in detail above with respect to FIG. 4.

Figure 10:
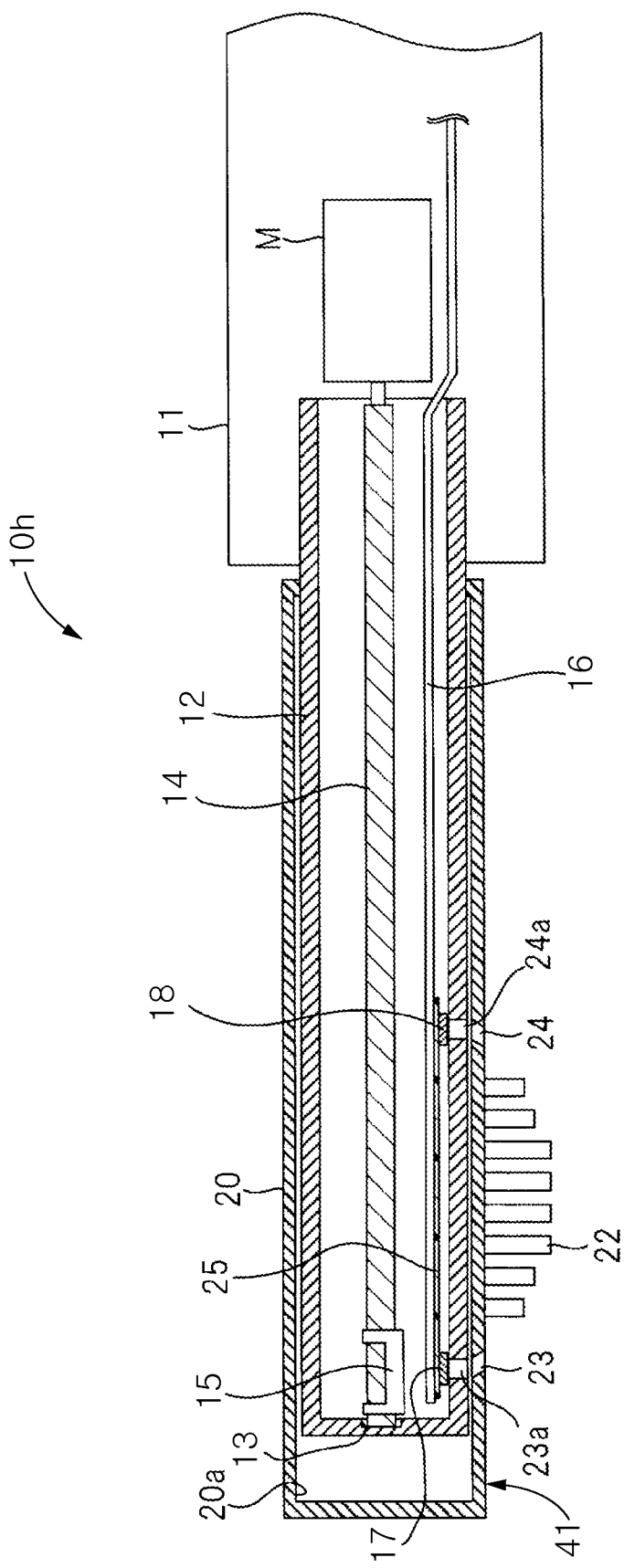
FIG. 10 is a schematic cross sectional view of an electric toothbrush in accordance with an eighth embodiment of the present invention.

FIG. 10 shows a cross section of another exemplified embodiment of an electric toothbrush 10*h*. In FIG. 10, the same numerals are given to similar components as those shown and described in conjunction with FIG. 5, and the descriptions of such similar components are omitted. In this embodiment of the electric toothbrush 10*h*, the light transmitting part 23 and the light receiving part 24 are fixed on the isolating member 25, and the isolating member 25 is fixed to the substrate 16 in a similar manner as described above for the embodiment shown in FIG. 8. In this embodiment of the electric toothbrush 10*h*, the shape of the bristle field formed by the tooth cleaning elements 22 is formed so that the tooth cleaning elements 22 nearest the light transmitting part 23 and those nearest the light receiving part 24 are shorter than those tooth cleaning elements closer to the middle portion of the bristle field, in a manner such as is described in detail above with respect to FIG. 5.

Figure 11:
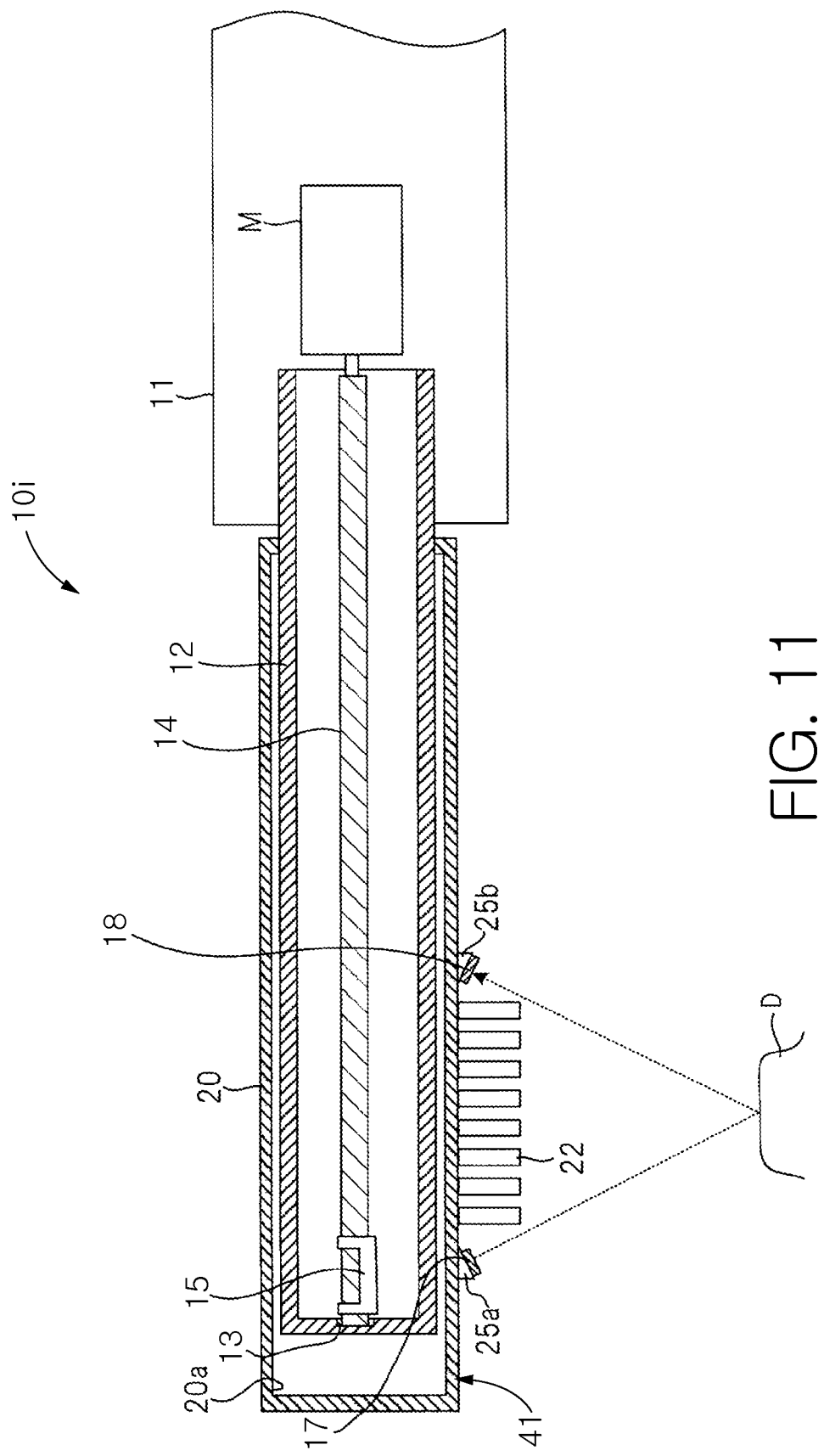
FIG. 11 is a schematic cross sectional view of an electric toothbrush in accordance with a ninth embodiment of the present invention.

FIG. 11 shows a cross section of another exemplified embodiment of an electric toothbrush 10*i*. In FIG. 11, the same numerals are given to similar components as those shown and described in conjunction with FIG. 6, and the descriptions of such similar components are omitted. In this embodiment of the electric toothbrush 10*i*, the light emitting element 17 and the light receiving element 18 are fixed on respective isolating members 25*a*, 25*b*, and the isolating members 25*a*, 25*b* are fixed to the front surface 41 of the brush unit 20. The function of the isolating members 25*a*, 25*b* are the same as the isolating member 25 described above with respect to FIG. 8.

As discussed above, in certain embodiments, the controller 90 may alternate between the first drive mode and the second drive mode. In certain of these embodiments, the controller may also drive the light emitting element 17 so that the light emitting element 17 emits light only during the first drive mode. When the first drive mode is active, the path of light emitted from the light transmitting part 23 and received by the light receiving part 24 is always a constant straight line in the planar view of FIG. 1, and that path does not substantially move in the plane formed of the tooth cleaning elements 122. This is because, as described above, during the first drive mode, the oscillations of the oscillating assembly (the stem 12 and the brush unit 20) are parallel to the pressing direction of the tooth cleaning elements 122. On the other hand, when the second drive mode is active, the path is not a constant straight line in the planar view of FIG. 1. This is because, as described above, during the second drive mode, the oscillations of the oscillating assembly are in a second direction that is different from the pressing direction, such that at least part of the oscillations during the second drive mode is not parallel to the pressing direction. Thus, during the second drive mode, there is the possibility of decreasing the detection accuracy of plaque. Therefore, by operating the light transmitting part 23 and the light receiving part 24 only when the first drive mode is active, plaque and the like on the teeth D may be more accurately detected.

In certain embodiments, the controller 90 may control the light emitting element 17 to emit light during both the first drive mode and during the second drive mode. In such embodiments, the controller 90 may process the output signal from the light receiving element 18 to detect plaque and the like only when the first drive mode is active. In this manner, plaque may still be more accurately detected.

In addition, as described above, when the second drive mode is active, there is a possibility that a portion of the tooth cleaning elements 122 will overlap the light transmitting part 23 and the light receiving part 24 in a planar view. Therefore, it may be particularly effective for the controller 90 to perform the plaque detection process only when the first drive mode is active.

In certain embodiments, the second drive mode may create oscillations in one of a plurality of different directions, with each oscillation direction being different from, and intersecting, the pressing direction. In such embodiments, the controller 90 may select any one of the oscillation directions for the second drive mode when alternating between the first drive mode and the second drive mode.

As discussed above, in embodiments which employ the isolating member 25, the isolating member may be formed from a material having a resonant frequency different from one or both of the oscillation frequencies of the first drive mode and the second drive mode for driving the oscillating assembly.

Figure 12:
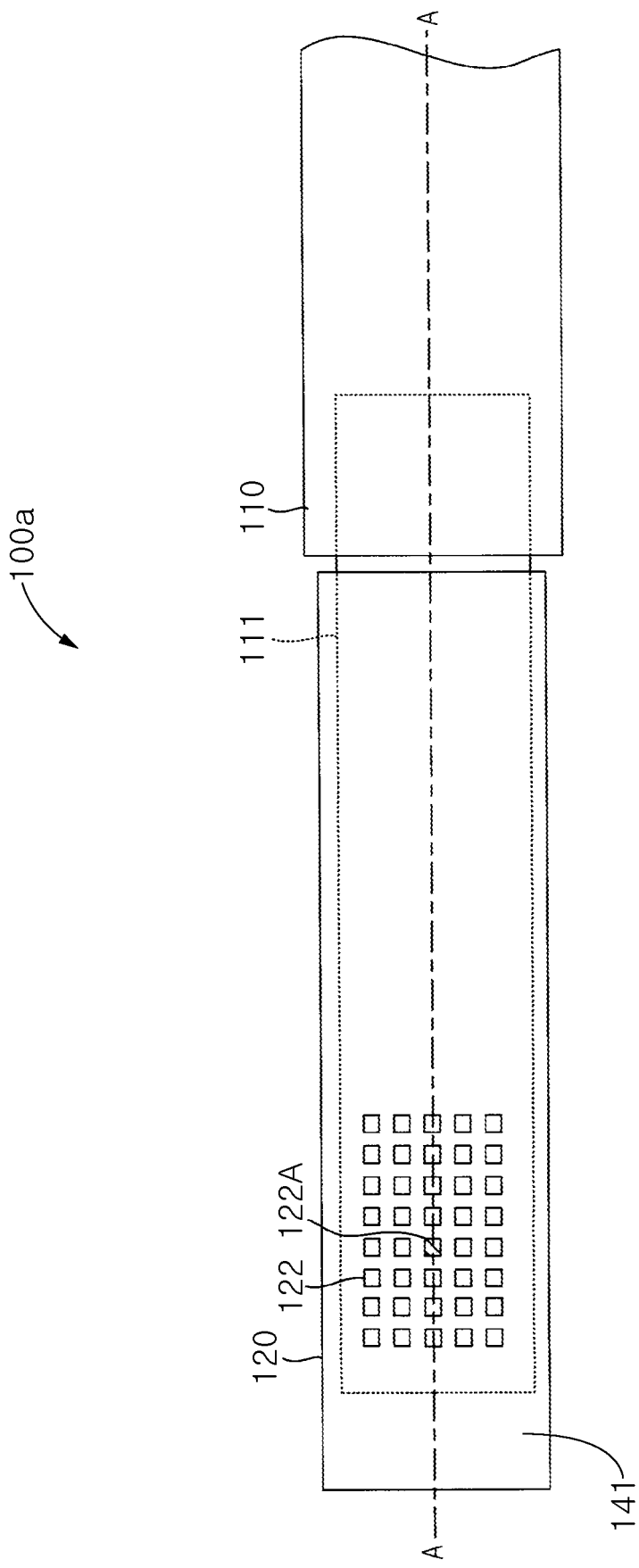
FIG. 12 is a top view of an electric toothbrush in accordance with a tenth embodiment of the present invention.
Figure 13:
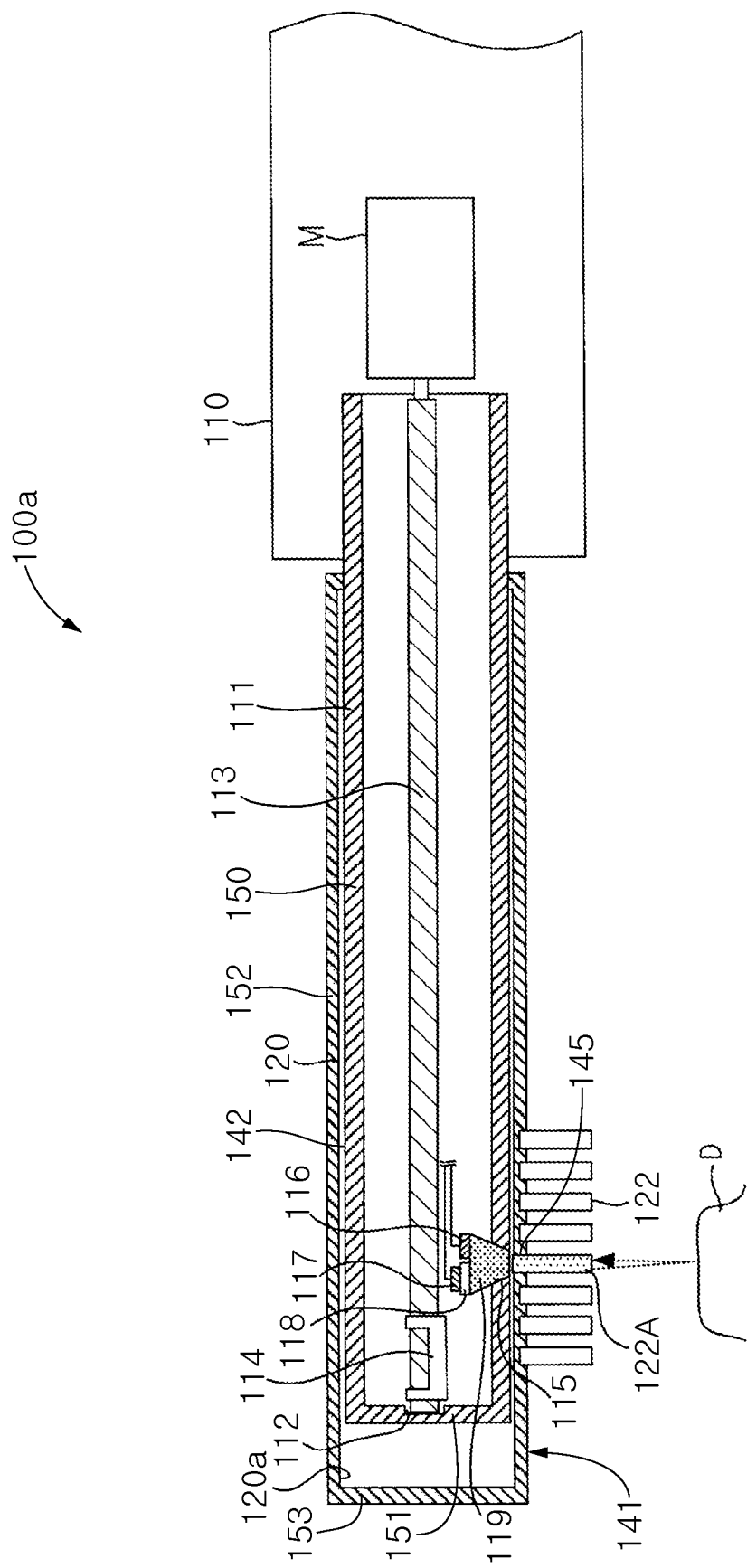
FIG. 13 is a schematic cross sectional view taken along line A-A in FIG. 12.

Alternative embodiments of an electric toothbrush for improving the detection of plaque and the like on teeth are illustrated in FIGS. 12-17. Unless expressly or impliedly contraindicated, the considerations and alternatives discussed above for other embodiments may apply equally to the embodiments of FIGS. 12-17. Referring to FIGS. 12 and 13 concurrently, an electric toothbrush 100*a* is shown in accordance with an embodiment of the present invention. FIG. 12 is a planar view illustrating a schematic configuration of the electric toothbrush 100*a* viewed from the brush pressing direction, and FIG. 13 is a cross-sectional view taken along line A-A of FIG. 12.

The electric toothbrush 100*a* includes a gripping part 110 that includes a battery and an electric control system therein, as well as a main body having a stem 111 fixed to the gripping part 110, and a brush unit 120 that can be detached from the stem 111. The stem 111 extends from the gripping part 110 and forms the portion of the electric toothbrush 100*a* to which the interior hollow part 120*a* of the brush unit 120 may be coupled. The brush unit 120 may be repetitively coupled to and detached from the stem 111 as necessary or desired. The brush unit 120 and the stem 111 may also include corresponding structures that facilitate locking the brush unit 120 to the stem 111. Thus, the gripping part 110 and the stem 111 may be reused with different brush units 120 having different structural arrangements to achieve different purposes. Furthermore, the brush unit 120 may be replaced when the tooth cleaning elements thereon are worn or splayed over time.

The brush unit 120 includes a front surface 141 and an opposite rear surface 142. Furthermore, the brush unit 120 includes a plurality of tooth cleaning elements 122 extending from the front surface 141. One of the tooth cleaning elements 122*a* (the one with an oblique profile) also functions as a detecting part for detecting plaque, tartar, tooth decay, and the like. The plurality of tooth cleaning elements 122 are depicted in various aligned columns and rows, although the invention is not to be so limited. The number, pattern, configuration, and structure of the tooth cleaning elements 122 is not to be limited in all embodiments. In certain embodiments, the tooth cleaning elements 122 are formed by a plurality of bristles that are bundled together into tufts that are then coupled to a head of the brush unit 120.

From among the tooth cleaning elements 122 extending from the outer peripheral face of the brush unit 120, one end of each tooth cleaning elements 122, not including the tooth cleaning elements 122A, is inserted into a concave receptacle formed on the front surface 141 of the brush unit 120. The fixed ends of the tooth cleaning elements 122 may be adhered and fixed with the concave receptacles of the brush unit 120 by an adhesive. Of course, the invention is not to be so limited, as the tooth cleaning elements 122 may be coupled to the head using staple technology, anchor-free tufting technologies, in-mold tufting technologies, or any other technology now known or later discovered. The tooth cleaning elements 122 may include bristles alone, bristles in combination with lamella formed of an elastomeric material, only bristles formed of an elastomeric material, or the like. The invention is not to be particularly limited by the specific details of the bristles unless specifically claimed as such. As discussed above, in certain embodiments the brush unit 120 may be detachable from the stem 111 and replaceable as needed when the tooth cleaning elements 122 thereon become frayed from use.

The fixed end of the tooth cleaning element 122A extending from the front surface 141 of the brush unit 120 is inserted into a hole 145 included in the front surface 141 of the brush unit 20. The fixed end of the tooth cleaning element 122A is adhered within this hole by an adhesive. In this manner, the fixed end of the tooth cleaning element 122A is exposed on the interior of the hollow part 120a of the brush unit 120, whereas the fixed ends of the other tooth cleaning elements 122, other than the tooth cleaning element 122A, are not exposed on the interior of the hollow part 120a of the brush unit 120. There is a possibility of water infiltrating in the hollow part 120a between the brush portion 122A and the hole provided on the housing of the brush unit 120. Because of this, it is preferable to use an adhesive that also serves to provide waterproofing as the adhesive that adheres this hole 145 and the brush portion 22A.

As is shown in FIG. 13, the brush unit 120 includes a cylindrical housing 150 with the tip end 151 being closed to form a hollow part 120a. The stem 111 includes a tube shaped housing 152 with the tip end 153 closed. By fitting the stem 111 into the hollow part 120a, the main body unit and the brush unit 120 may be coupled together. The stem 111 includes a bearing 112 formed on the interior surface of the tip end 153. One end of an eccentric shaft 113 is inserted into the bearing 112, and a weight 114 is coupled to the eccentric shaft 113. The other end of the eccentric shaft 113 is linked to a rotary shaft of the motor M built in the gripping part 110. By rotating the rotary shaft of the motor M, the eccentric shaft 113 rotates. The weight 114 is fixed to the eccentric shaft 113 in the vicinity of the bearing 112. Due to this weight 114, the center of gravity of the eccentric shaft 113 is shifted from the center of rotation. The motor M may be controlled by a controller, such as in any manner discussed above, to oscillate the stem 111 and the brush unit 120. The oscillations may also be generated by other means.

The stem 111 also includes a light emitting element 116, a light receiving element 117, a band pass filter 118, and a light guide 119. The light emitting element 116, the light receiving element 117, and the band pass filter 118 are fixed to the light guide 119. The light emitting element 116 includes a light emitting diode (LED), a laser diode, or the like. The invention is not to be so limited, as other types of light generating devices may be used for the light emitting element 116. The wavelength of light emitted from the light emitting element 116 may be appropriately selected according to the elements in the mouth (plaque, tartar, tooth decay, and the like) to be detected. For example, when detecting plaque, a light emitting element 116 is used that emits blue light. The light emitting element 116 is connected to a controller, such as is described above with reference to FIGS. 1 and 2, built in the gripping part 110 by a lead wire. The light receiving element 117 includes a light sensing element, such as a photo diode or the like, that converts light into an electric signal. The invention is not to be so limited, as other types of light sensing elements may be used for the light receiving element 117. The light receiving element 117 is connected with the controller built in the gripping part 10 by a lead wire or the like.

The band pass filter 118 is included to spectrally limit the wavelength of light received by the light receiving element 117. For example, when the electric toothbrush has a function of detecting plaque, the band pass filter 118 may include a filter characteristic where blue light emitted from the light emitting element 116 is blocked, and red light generated by the plaque, in response to the incident blue light, is allowed to pass.

The light guide 119 has an end portion fitted to the hole 115 of the stem 111 so that the end portion of the light guide 119 is positioned opposite the end of the tooth cleaning element 122a that is exposed within the hollow part 120A of the brush unit 120. The light guide 119 guides light emitted from the light emitting element 116 to the tooth cleaning element 122A, and it guides light received from the tooth cleaning element 122A to the light receiving element 117 via the band pass filter 118. The light guide 119 passes light emitted from the light emitting element 116, and it is therefore formed of a material that passes light that is to be sensed by the light receiving element 117. Examples of material that may be used for the light guide 119 include, for example, acryl, polycarbonate, of the like. The light guide 119 may also include a metal film deposited on its surfaces, excluding the surface opposing the tooth cleaning element 122A and the surface passing light to the light emitting element 16 and the band pass filter 18. The inclusion of the metal film helps to prevent light entering the light guide 119 from leaking to the exterior of the light guide 119, except for in the two aforementioned locations.

During operation, the controller controls the operation of light emitted from the light emitting element 116. For example, as discussed above, the controller, may control the light emitting diode 116 to alternate between a first drive mode and a second drive mode. The controller in this embodiment may control the light emitting element 116 and the light receiving element 117 in any of the manners previously discussed. When light is emitted from the light emitting element 116, the light guide 119 guides the light into the end of the tooth cleaning element 122A exposed within the hollow part 120a of the brush unit 120. Light that has entered the tooth cleaning element 122A proceeds to the free tip end of the tooth cleaning element 122A. In embodiments in which the tooth cleaning element 122A is formed of a plurality of fibers, light entering the tooth cleaning element 122A proceeds to the free tip end of each of the fibers of the tooth cleaning element 122A. At the free tip end of the tooth cleaning element 122A, the light is emitted to the exterior of the tooth cleaning element 122A. The light emitted from the tooth cleaning element 122A is incident on the surface of a tooth D on the site where the plurality of tooth cleaning elements 122 are pressed.

During uses when blue light is emitted from the light emitting element 116, when the blue light is incident on the surface of a tooth D where there is plaque, the plaque will generate a red light in response to the incident blue light. Red light emitted from the plaque enters the tooth cleaning element 122A and is received by the light guide 119, which guides the received light to the band pass filter 18. Because red light can pass through the band pass filter 18, the red light is received by the light receiving element 117. The light receiving element 117 converts the received red light into an electric output signal, which is communicated to the controller. The controller determines the amount of plaque on the tooth D by analyzing the output signal from the light receiving element 117. The controller may then notify the user, using the notification part discussed above, concerning the amount of plaque detected on the tooth D. By this process, it is possible to sense plaque adhering to the site on the tooth D against which the tooth cleaning element 122A is pressed, so that the user may be notified in real-time about the amount of plaque detected on the tooth D.

An advantage of the electric toothbrush 100a of FIGS. 12-13 is that the brush portion 122A is employed both for sensing plaque and for brushing the teeth to remove plaque. Because of this, it is possible to sense plaque adhered to a tooth being brushed without reducing the number of tooth brushing elements on the front surface 141 of the brush unit 120, thereby eliminating the need to make the brush unit 120 larger to accommodate the light emitting and light sensing functionality.

As another advantage of the electric toothbrush 100a of FIGS. 12-13 is that the brush unit 120 is a simple configuration in which tooth cleaning elements 122 include only one portion that is configured as the tooth cleaning element 122A. Moreover, in certain embodiments, the tooth cleaning element 122A may be formed of the same material the rest of the tooth cleaning elements 122. Thus, the differences between the brush unit 120 and a conventional brush unit is minimized. Because of this, manufacturing costs of the brush unit 120 can be reduced. Also, because the brush unit 20 is expendable, the benefits of reducing manufacturing costs are very large.

It is to be noted that in the exemplified embodiment of FIGS. 12-13, the fixed end of the tooth cleaning element 122A is physically exposed within the hollow part 120a of the brush unit 120. However, the fixed end of the tooth cleaning element 122A may be optically exposed within the hollow part 20a of the brush unit 120. The fixed end being optically exposed refers to a state where the fixed end can be seen from the hollow part 20a by light at the wavelength emitted from the light emitting element 116 and by light at the wavelength to be received by the light receiving element 117.

Figure 14:
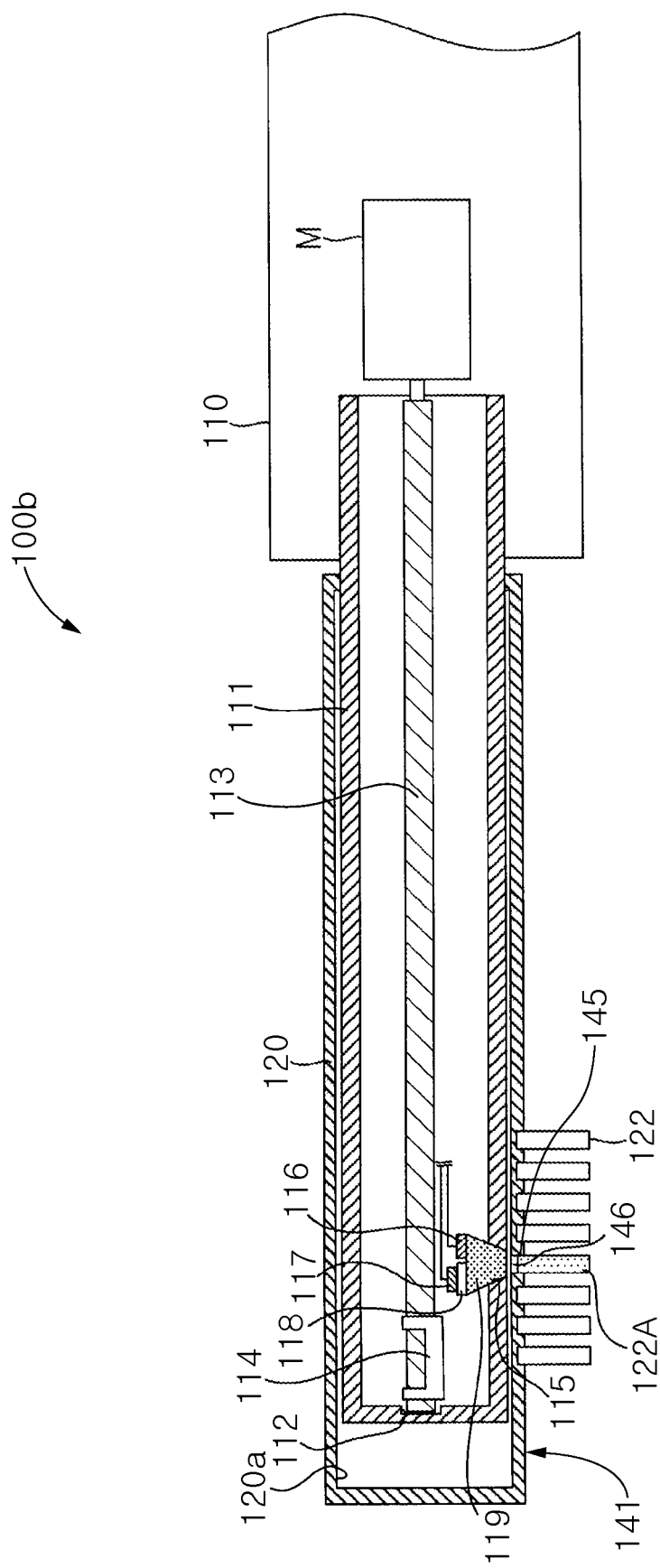
FIG. 14 is a schematic cross sectional view of an electric toothbrush in accordance with an eleventh embodiment of the present invention.

FIG. 14 shows a cross section of another exemplified embodiment of an electric toothbrush 100b. In FIG. 14, the same numerals are given to similar components as those shown and described in conjunction with FIGS. 12-13, and the descriptions of such similar components are omitted. In this embodiment of the electric toothbrush 100b, one portion of the hole 145, on the side of the hollow part 120a of the brush unit 120, included in the front surface 141 of the brush unit 120 is filled by a material 146 that is transparent to light in the operational wavelength of the electric toothbrush 100b. The fixed end of the tooth cleaning element 122A is adhered and fixed within the hole 145 by an adhesive transparent to light in the operational wavelength. With this configuration, the fixed end of the tooth cleaning element 122A is optically exposed within the hollow part 120a.

An advantage of the electric toothbrush 100b of FIG. 14 is that manufacturing costs can be reduced because the tooth cleaning elements 122 included as part of the brush unit 120 can all have the same dimensions. Furthermore, as compared to the electric toothbrush 100a shown in FIG. 13, the waterproofing of the electric toothbrush 100b is improved because the presence of the material 146 in the hole 145 prevents water from infiltrating into the hollow part 120a of the brush unit 120.

Above, an exemplified embodiment is described in which only one of the tooth cleaning elements 122, namely tooth cleaning element 122A, included on the brush unit 120 serves to transmit and receive light to detect plaque and the like on teeth. The invention is not so limited, as a plurality of the tooth cleaning elements 122 may serve to transmit and receive light for detection of plaque and the like.

Figure 15:
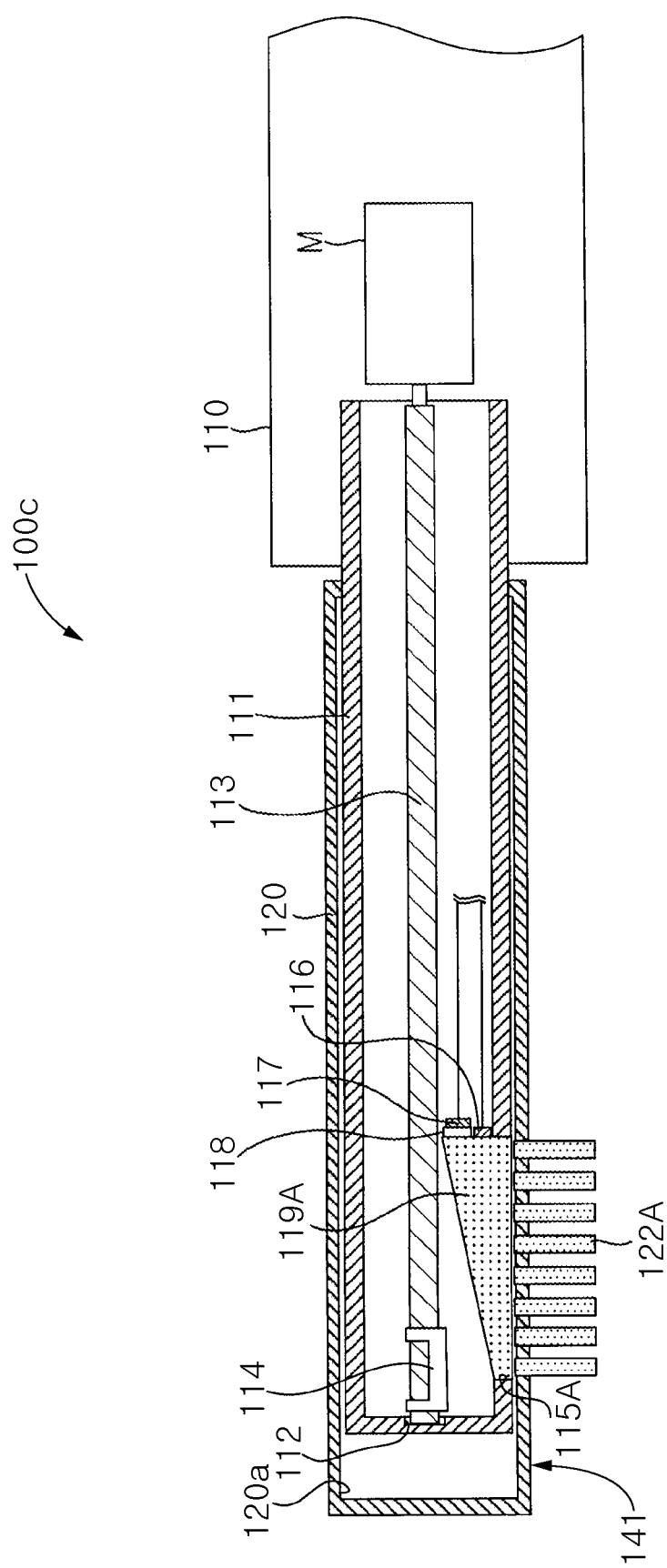
FIG. 15 is a schematic cross sectional view of an electric toothbrush in accordance with a twelfth embodiment of the present invention.

FIG. 15 shows a cross section of another exemplified embodiment of an electric toothbrush 100c. In FIG. 15, the same numerals are given to similar components as those shown and described in conjunction with FIGS. 12-13, and the descriptions of such similar components are omitted. In this embodiment of the electric toothbrush 100c, all of the tooth cleaning elements 122A transmit and receive light for detecting plaque and the like on a tooth. In this embodiment, a light guide 119A is positioned in the interior of the stem 111 within a hole 115A formed in the stem 111. The light guide 119A guides light emitted from the fixed end of each tooth cleaning element 122A to the light receiving element 117 via the band pass filter 118. The light guide 119A also guides light emitted from the light emitting element 116 to the fixed ends of each tooth cleaning element 122A. In this manner, plaque detection accuracy can be raised because all of the tooth cleaning elements 122A transmit and receive the light used for detecting plaque and the like.

In certain embodiments which include multiple tooth cleaning elements 122A for transmitting and receiving light, each tooth cleaning element 122A may be associated with a separate light guide 119, light emitting element 116, light receiving element 117, and band pass filter 118, such that the stem 111 includes multiple ones of each of the light guide 119, the light emitting element 116, the light receiving element 117, the and band pass filter 118. In such embodiments, even if one of the plurality of tooth cleaning elements 122A breaks, plaque sensing can still continue. Additionally, by sensing the amount of plaque using several independent sub-systems, the accuracy of detecting plaque can be improved.

Figure 16:
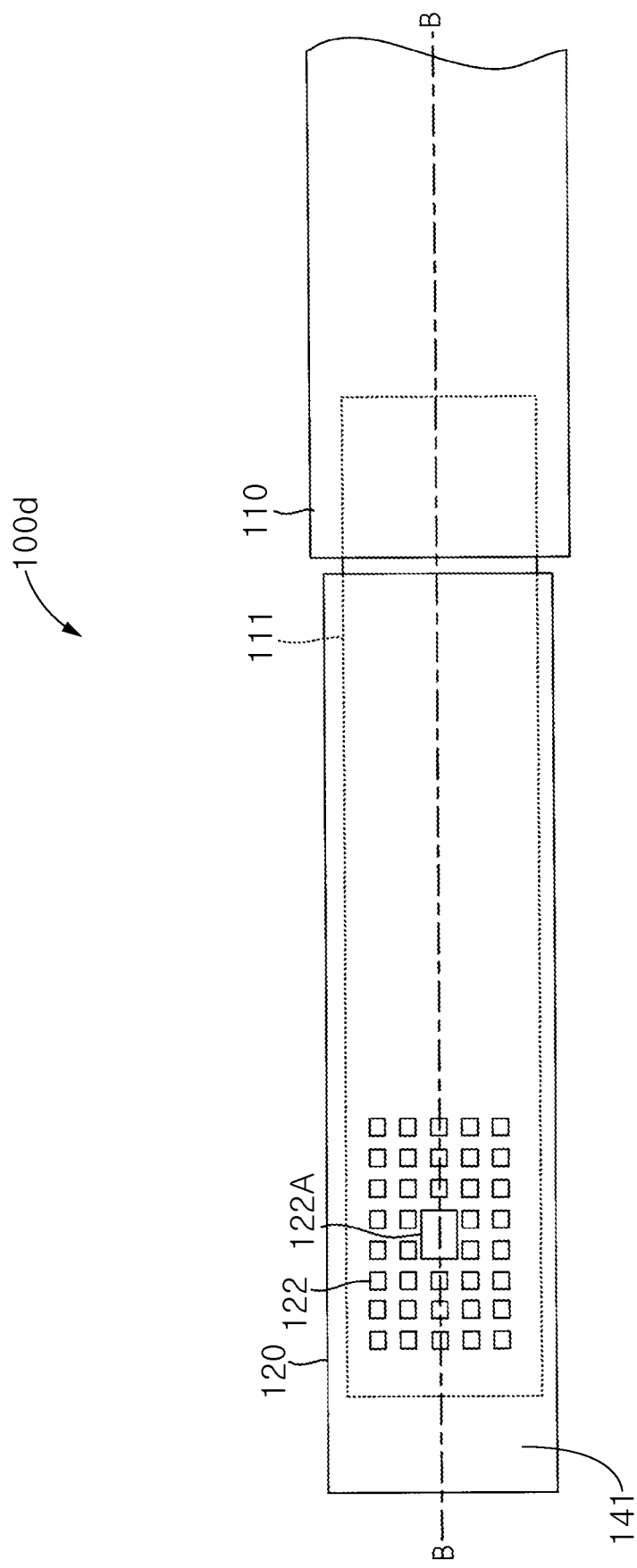
FIG. 16 is a schematic cross sectional view of an electric toothbrush in accordance with a thirteenth embodiment of the present invention.
Figure 17:
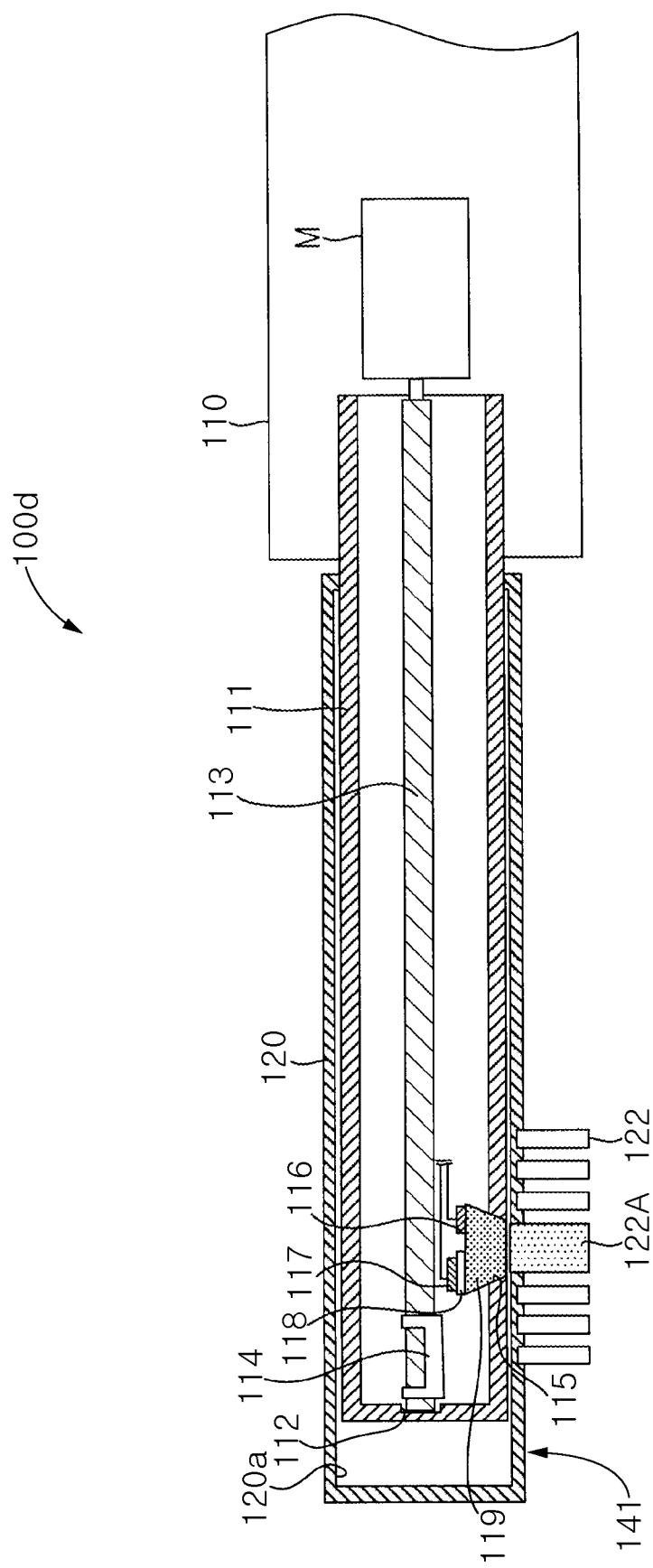
FIG. 17 is a schematic cross sectional view of an electric toothbrush in accordance with a fourteenth embodiment of the present invention.

FIGS. 16-17 show another exemplified embodiment of an electric toothbrush 100d. A top planar view is shown in FIG. 16, and the same numerals are given to similar components as those shown and described in conjunction with FIG. 12, with the descriptions of such similar components being omitted. In this embodiment of the electric toothbrush 100d, the surface area of the tooth cleaning element 122A included as part of the brush unit 120 is larger than the surface area of the tooth cleaning elements 122. As shown in FIG. 17, the width of the tooth cleaning element 122A is larger, and the width of the light guide 119 is larger, as compared to the embodiment of the electric toothbrush 100a shown in FIG. 13.

With the tooth cleaning element 122A having a larger surface area, the amount of light emitted toward a tooth can be increased and the amount of light received from the tooth (by reflection or induced emission) can be increased. Because of this, plaque detection accuracy can be improved.

In the exemplified embodiment of FIGS. 16-17, although there is only one tooth cleaning element 122A shown, it is to be understood that certain embodiments may include multiple tooth cleaning elements 122A.

In the embodiments described above, each have the light guide 119, the light emitting element 116, the light receiving element 117, and the band pass filter 118 positioned within the interior of the stem 111. In certain embodiments, these components may be positioned on the outer peripheral face of the stem 111. The invention is not to be limited by the positioning of these components unless expressly stated in the claims. However, embodiments in which these components are on the interior of the stem 111 are preferred because doing so enables the stem 111 to be made smaller.

Similarly, in the embodiments described above, each have the light emitting element 116, the light receiving element 117, and the band pass filter 118 positioned within the interior of the stem 111. In certain embodiments, these components may be positioned in the gripping part 110. In such embodiments, an optical fiber is included extending from the interior of the stem 111 to the gripping part 110. By way of example, a first optical fiber may be included which has one end receiving light from the light emitting element 116 and the other end transmitting light to the light guide 119, and a second optical fiber may be included which has one end receiving light from the light guide 119 and the other end transmitting light to the light receiving element 117. The band pass filter 118 may be located between the second optical fiber and the light guide 119 or between the second optical fiber and the light receiving element 117. In such embodiments, the light guide 119 and the two optical fibers function as the light guide. With such a configuration, an improvement of plaque detection accuracy can be expected because the light receiving element 117 would be less affected by the oscillation of the stem 111. Alternatively, a single optical fiber could be used instead of the two optical fibers.

For the embodiments shown and described in connection with FIGS. 12-17, in which the light emitting element 116 and the light receiving element 117 are included as part of the stem 111, the loss of light within the mouth can be minimized, thereby increasing the amount of light which is received by the light receiving element 17. Because of this, an improvement in plaque detection accuracy can be expected.

Also, in the embodiments shown and described in connection with FIGS. 12-17, the tooth cleaning element 122A, or alternatively each fiber forming part of the tooth cleaning element 122A, needs to be formed of an optical transmission material which is at least transparent to light emitted from the light emitting element 116 and light to be received by the light receiving element 117. In certain embodiments, these properties may be met by selecting from among materials that are currently used generally for toothbrushes. In this manner, manufacturing costs may be reduced.

In certain embodiments the exposed longitudinal surfaces of the tooth cleaning element 122A, excluding the tip end, or alternatively each fiber forming part of the tooth cleaning element 122A, may be coated to prevent light from escaping to the exterior through parts of the tooth cleaning element 122A other than the tip end. For example, a coating of polyetrafluoroethylene (PTFE) or the like may be applied on the peripheral face of the tooth cleaning element 122A. With this configuration, plaque sensing accuracy can be improved.

In certain embodiments, the electric toothbrush may be of the type that removes plaque by rotating a platform to which the tooth cleaning elements are coupled. In such embodiments, the tooth cleaning element 122A may be positioned at the center of rotation of the platform. Plaque can therefore also be accurately detected in such embodiments.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An electric toothbrush comprising:
   a main body comprising:
   a stem having a hole;
   a light emitting element;
   a light receiving element; and
   a light guide optically coupled to the light emitting element and to the light receiving element; and
   a brush unit coupled to the main body, the brush unit comprising:
   a housing forming a hollow part and having a front surface with a through hole, the hollow part configured to be seated on the stem of the main body;
   a plurality of tooth cleaning elements coupled to and extending from the front surface, the plurality of tooth cleaning elements including at least a first tooth cleaning element formed of an optical transmission material, wherein when the hollow part of the brush unit is seated on the stem of the main body, the light guide is optically coupled to the first tooth cleaning element such that light emitted from the light emitting element is guided out a tip end of the first tooth cleaning element and light received into the tip end of the first tooth cleaning element is guided to the light receiving element;
   wherein an end portion of the light guide is fitted to the hole of the stem and the first tooth cleaning element extends into the through hole in the front surface of the housing so that a fixed end of the first tooth cleaning element is exposed to an interior of the hollow part of the housing, the fixed end of the first tooth cleaning element positioned opposite to and facing the end portion of the light guide.

2. The electric toothbrush according to claim 1, wherein the main body further comprises a band pass filter optically coupled between the light receiving element and the light guide.

3. The electric toothbrush according to claim 1, wherein the main body further comprises a drive assembly, the drive assembly configured to generate oscillations.

4. The electric toothbrush according to claim 1, wherein the main body further comprises a processor operatively coupled to the light receiving element, and the light receiving element provides an output signal to the processor in response to light incident on the light receiving element.

5. The electric toothbrush according to claim 1, wherein the light emitting element and the light receiving element are positioned within the stem.

6. The electric toothbrush according to claim 1, wherein the plurality of tooth cleaning elements includes a second tooth cleaning element formed of the optical transmission material and extending to the interior of the housing, wherein when hollow part of the brush unit is seated on the stem of the main body, the light guide is optically coupled to the second tooth cleaning element such that light emitted from the light emitting element is guided out a tip end of the second tooth cleaning element and light received into the tip end of the second tooth cleaning element is guided to the light receiving element.

7. The electric toothbrush according to claim 1, wherein each of the plurality of tooth cleaning elements are formed of the optical transmission material.

8. The electric toothbrush according to claim 1, wherein the first tooth cleaning element comprises a plurality of fibers.

9. The electric toothbrush according to claim 8, wherein each of the plurality of fibers comprises a surface coating on exposed longitudinal surfaces of the fiber.

10. The electric toothbrush according to claim 1, wherein each of the plurality of tooth cleaning elements are operably coupled to the light guide, the light guide being configured to guide light emitted from fixed ends of each of the plurality of tooth cleaning elements to the light receiving element and to guide light emitted from the light emitting element to the fixed ends of each of the plurality of tooth cleaning elements.

11. The electric toothbrush according to claim 1 further comprising a material that is transparent to light in an operational wavelength of the light emitting element filling in a portion of the through hole that is adjacent to the interior of the hollow part of the housing.

12. An electric toothbrush comprising:
a brush unit comprising a housing having a hollow part; and
a main body comprising a stem, the hollow part of the brush unit being configured to seat on the stem; wherein:
the brush unit comprises a front surface and a plurality of tooth cleaning elements extending from the front surface in a pressing direction;
at least a first tooth cleaning element of the plurality of tooth cleaning elements is formed of an optical transmission material, the first tooth cleaning element including a fixed end coupled to the front surface of the brush unit and exposed within the hollow part of the brush unit; and
the main body unit comprises a light emitting element which emits light, a light receiving element which generates an output signal in response to received light, a light guide which guides light from the light emitting element to the fixed end of the first tooth cleaning element and which guides light from the fixed end of the first tooth cleaning element to the light receiving element, and a processor which receives the output signal from the light receiving element;
wherein the light guide is positioned within the stem such that when the brush unit is seated on the stem, the light guide is positioned opposite the first tooth cleaning element, and the light emitting element and the light receiving element are positioned within the stem.

13. The electric toothbrush according to claim 12, wherein each of the plurality of tooth cleaning elements are formed of the optical transmission material.

14. The electric toothbrush according to claim 12, wherein
the first tooth cleaning element is formed of a plurality of fibers; and
each of the plurality of fibers comprises a surface coating on exposed portions of each fiber, except a tip end, to prevent light passing through each fiber from leaking to the outside.

15. The electric toothbrush according to claim 12, wherein:
more than one of the tooth cleaning elements are formed of the optical transmission material; and
in a plane perpendicular to the pressing direction, the tooth cleaning elements formed of the optical material have a greater cross sectional area than the remainder of the tooth cleaning elements.

* * * * *